United States Patent
Moon et al.

(10) Patent No.: US 10,408,754 B2
(45) Date of Patent: Sep. 10, 2019

(54) METHOD OF MEASURING A TARGET, SUBSTRATE, METROLOGY APPARATUS, AND LITHOGRAPHIC APPARATUS

(71) Applicant: ASML Netherlands B.V., Veldhoven (NL)

(72) Inventors: Euclid Eberle Moon, San Jose, CA (US); Arie Jeffrey Den Boef, Waalre (NL)

(73) Assignee: ASML Netherlands B.V., Veldhoven (NL)

( * ) Notice: Subject to any disclaimer, the term of this patent is extended or adjusted under 35 U.S.C. 154(b) by 49 days.

(21) Appl. No.: 15/654,813

(22) Filed: Jul. 20, 2017

(65) Prior Publication Data
US 2018/0024054 A1    Jan. 25, 2018

Related U.S. Application Data

(60) Provisional application No. 62/400,360, filed on Sep. 27, 2016, provisional application No. 62/394,457, (Continued)

(51) Int. Cl.
*G06K 9/00*     (2006.01)
*G01N 21/47*    (2006.01)
(Continued)

(52) U.S. Cl.
CPC ............ *G01N 21/47* (2013.01); *G01N 21/88* (2013.01); *G03F 7/70633* (2013.01); *G03F 7/70683* (2013.01); *G03F 9/7026* (2013.01)

(58) Field of Classification Search
CPC .... G01N 21/47; G01N 21/88; G03F 7/70633; G03F 7/70683; G03F 9/7026
See application file for complete search history.

(56) References Cited

U.S. PATENT DOCUMENTS

| | | |
|---|---|---|
| 4,200,395 A | 4/1980 | Smith et al. |
| 5,414,514 A | 5/1995 | Smith et al. |

(Continued)

FOREIGN PATENT DOCUMENTS

| | | |
|---|---|---|
| EP | 1739493 A1 | 1/2007 |
| WO | WO 2009078708 A1 | 6/2009 |

(Continued)

OTHER PUBLICATIONS

Moon, E., "Interferometric-Spatial-Phase Imaging for Sub-Nanometer Three-Dimensional Positioning," MIT Sep. 2004; 206 pages.

(Continued)

*Primary Examiner* — Bhavesh M Mehta
*Assistant Examiner* — Ian L Lemieux
(74) *Attorney, Agent, or Firm* — Stern, Kessler, Goldstein & Fox P.L.L.C.

(57) ABSTRACT

Disclosed is a method of measuring a target, an associated substrate, a metrology apparatus and a lithographic apparatus. In one arrangement the target comprises a layered structure. The layered structure has a first target structure in a first layer and a second target structure in a second layer. The method comprises illuminating the target with measurement radiation. Scattered radiation formed by interference between plural predetermined diffraction orders is detected. The predetermined diffraction orders are generated by diffraction of the measurement radiation from the first target structure and are subsequently diffracted from the second target structure. A characteristic of the lithographic process is calculated using the detected scattered radiation formed by the interference between the predetermined diffraction orders.

21 Claims, 25 Drawing Sheets

Related U.S. Application Data filed on Sep. 14, 2016, provisional application No. 62/365,142, filed on Jul. 21, 2016.

(51) Int. Cl.
  *G01N 21/88* (2006.01)
  *G03F 7/20* (2006.01)
  *G03F 9/00* (2006.01)

(56) References Cited

U.S. PATENT DOCUMENTS

| | | | |
|---|---|---|---|
| 5,808,742 A | 9/1998 | Everett et al. | |
| 6,088,103 A | 7/2000 | Everett et al. | |
| 6,522,411 B1 | 2/2003 | Moon et al. | |
| 7,247,843 B1 | 7/2007 | Moon | |
| 7,474,410 B2 | 1/2009 | Moon | |
| 7,535,581 B2 | 5/2009 | Moon | |
| 7,800,761 B2 | 9/2010 | Moon | |
| 9,235,141 B2* | 1/2016 | Van Der Schaar | G03F 7/70633 |
| 2004/0006757 A1* | 1/2004 | Chen | G03F 1/29 716/50 |
| 2006/0033921 A1 | 2/2006 | Den Boef et al. | |
| 2006/0066855 A1 | 3/2006 | Boef et al. | |
| 2010/0201963 A1 | 8/2010 | Cramer et al. | |
| 2010/0265506 A1* | 10/2010 | Den Boef | G03F 7/70633 356/399 |
| 2011/0027704 A1 | 2/2011 | Cramer et al. | |
| 2011/0043791 A1 | 2/2011 | Smilde et al. | |
| 2011/0069292 A1 | 3/2011 | Den Boef | |
| 2011/0073775 A1* | 3/2011 | Setija | G03F 7/70633 250/492.1 |
| 2011/0102753 A1 | 5/2011 | Van De Kerkhof et al. | |
| 2012/0044470 A1 | 2/2012 | Smilde et al. | |
| 2012/0123581 A1 | 5/2012 | Smilde et al. | |
| 2012/0242970 A1 | 9/2012 | Smilde et al. | |
| 2013/0258310 A1 | 10/2013 | Smilde et al. | |
| 2013/0271740 A1 | 10/2013 | Quintanilha | |
| 2014/0192338 A1 | 7/2014 | Den Boef | |
| 2015/0177135 A1* | 6/2015 | Amit | G01N 21/47 702/150 |
| 2019/0094702 A1* | 3/2019 | Shmarev | G03F 7/7065 |

FOREIGN PATENT DOCUMENTS

| | | |
|---|---|---|
| WO | WO 2009106279 A1 | 9/2009 |
| WO | WO 2011/012624 A1 | 2/2011 |
| WO | WO 2015/185166 A1 | 12/2015 |
| WO | WO 2016/030205 A1 | 3/2016 |
| WO | WO 2016083076 A1 | 6/2016 |

OTHER PUBLICATIONS

International Search Report and Written Opinion of the International Searching Authority, directed to related International Patent Application No. PCT/EP2017/067048, dated Oct. 20, 2017; 13 pages.

* cited by examiner

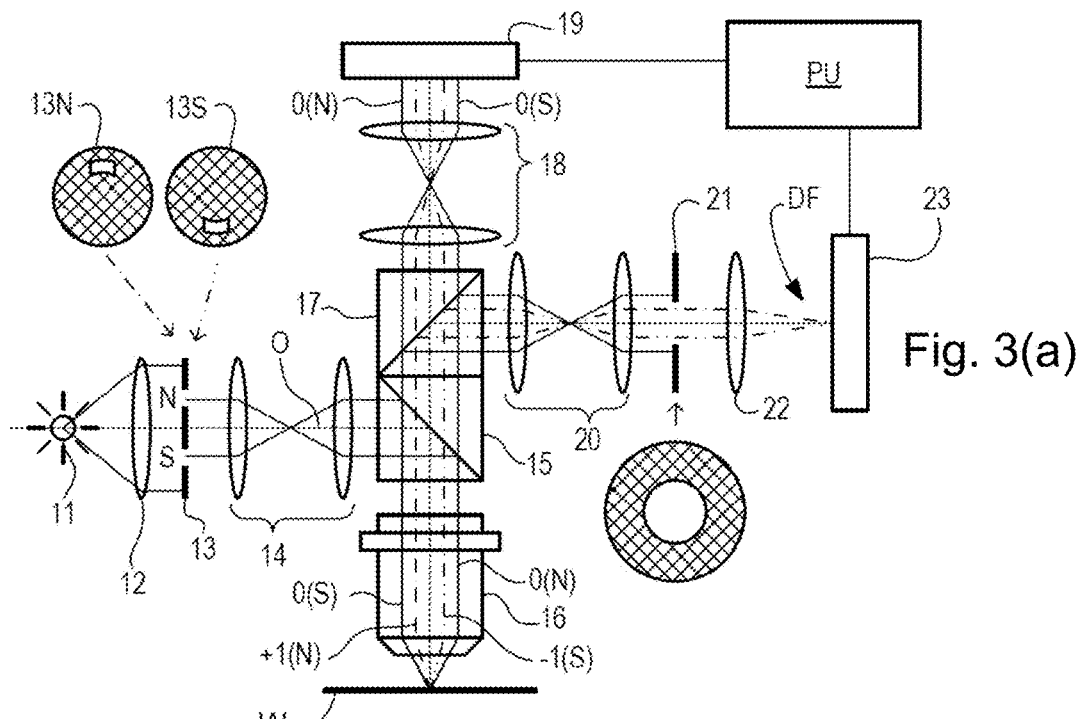
Fig. 3(a)
Fig. 3(b)
Fig. 3(c)   Fig. 3(d)
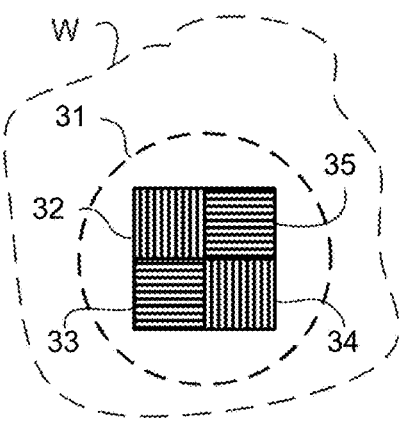
Fig. 4
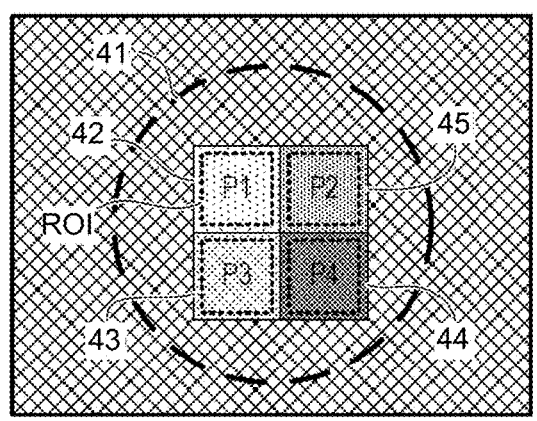
Fig. 5

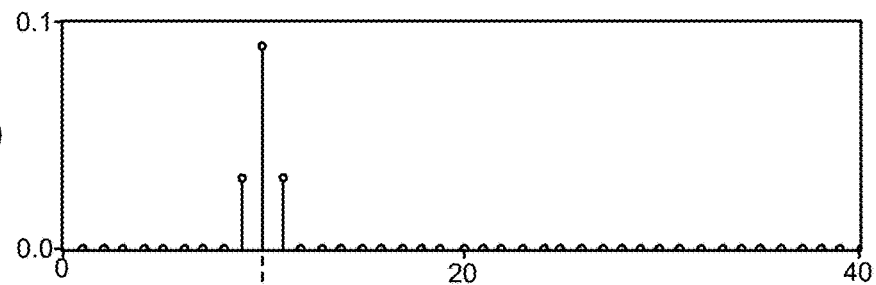
Fig. 17(a)
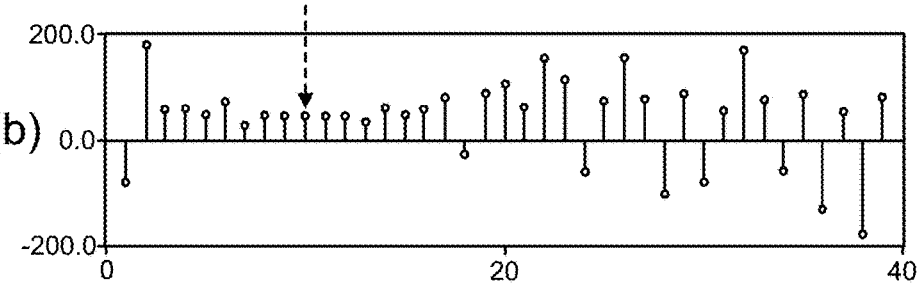
Fig. 17(b)
Fig.18
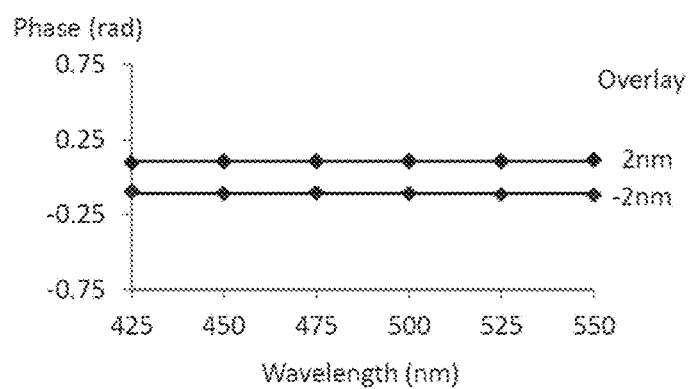
P1 = 450nm. P2 = 500nm.
Ph = 600nm.
Target 8um x 8um, Fig.19
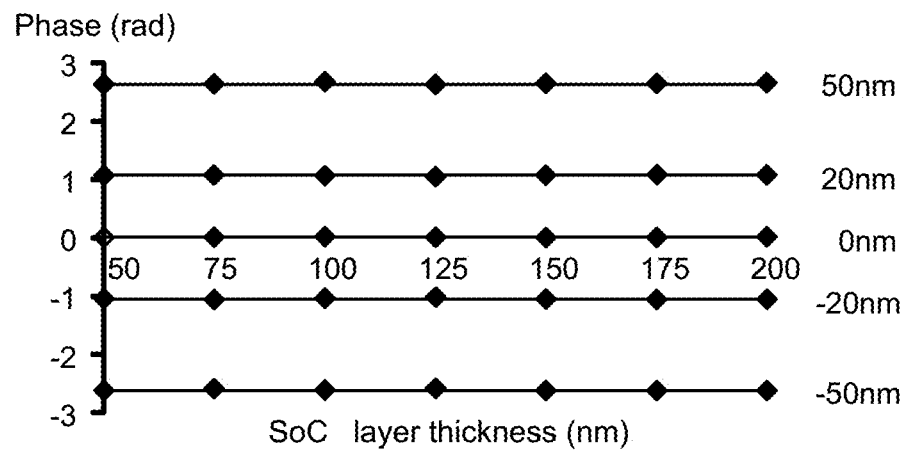
P1 = 450nm. P2 = 500nm.
Ph = 600nm.
Target 8um x 8um,
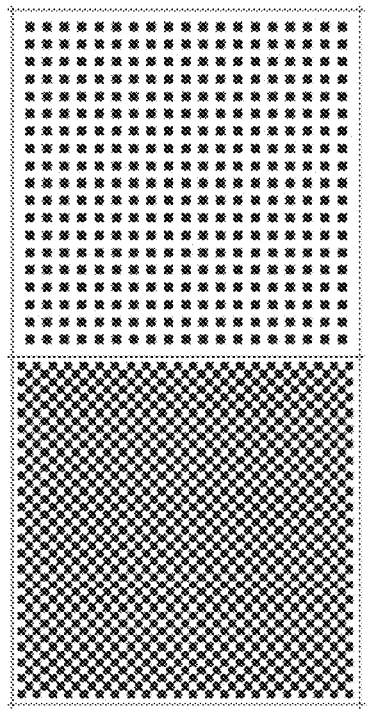
Fig. 20(a)
Fig. 20(b)

METHOD OF MEASURING A TARGET, SUBSTRATE, METROLOGY APPARATUS, AND LITHOGRAPHIC APPARATUS

This application incorporates herein by reference in their entireties U.S. Provisional Applications 62/365,142, filed Jul. 21, 2016, 62/394,457, filed Sep. 14, 2016, and 62/400,360, filed Sep. 27, 2016.

BACKGROUND

Field of the Invention

The present invention relates to methods and apparatus for metrology usable, for example, in the manufacture of devices by lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, a measure of the accuracy of alignment of two layers in a device. Overlay may be described in terms of the degree of misalignment between the two layers, for example reference to a measured overlay of 1 nm may describe a situation where two layers are misaligned by 1 nm.

Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target by iterative approaches such as rigorous coupled wave analysis or finite element methods; library searches; and principal component analysis.

The targets used by conventional scatterometers are relatively large, e.g., 40 μm by 40 μm, gratings and the measurement beam generates a spot that is smaller than the grating (i.e., the grating is underfilled). This simplifies mathematical reconstruction of the target as it can be regarded as infinite. However, in order to reduce the size of the targets, e.g., to 10 μm by 10 μm or less, e.g., so they can be positioned in amongst product features, rather than in the scribe lane, metrology has been proposed in which the grating is made smaller than the measurement spot (i.e., the grating is overfilled). Typically such targets are measured using dark field scatterometry in which the zeroth order of diffraction (corresponding to a specular reflection) is blocked, and only higher orders processed. Examples of dark field metrology can be found in international patent applications WO 2009/078708 and WO 2009/106279 which documents are hereby incorporated by reference in their entirety. Further developments of the technique have been described in patent publications US20110027704A, US20110043791A and US20120242970A. The contents of all these applications are also incorporated herein by reference. Diffraction-based overlay using dark-field detection of the diffraction orders enables overlay measurements on smaller targets. These targets can be smaller than the illumination spot and may be surrounded by product structures on a wafer. Targets can comprise multiple gratings which can be measured in one image.

In the known metrology technique, overlay measurement results are obtained by measuring an overlay target twice under certain conditions, while either rotating the overlay target or changing the illumination mode or imaging mode to obtain separately the −1st and the +1st diffraction order intensities. The intensity asymmetry, a comparison of these diffraction order intensities, for a given overlay target provides a measurement of target asymmetry, that is asymmetry in the target. This asymmetry in the overlay target can be used as an indicator of overlay error (undesired misalignment of two layers).

It has been found that changes in the manufacturing process of the semiconductor device can reduce the robustness or reliability of overlay error measurements.

It is an object of the invention to improve the robustness or reliability of measurements of a lithographic characteristic such as overlay error.

SUMMARY OF THE INVENTION

According to an aspect, there is provided a method of measuring a target formed by a lithographic process, the target comprising a layered structure having a first target structure in a first layer and a second target structure in a second layer, the method comprising: illuminating the target with measurement radiation; detecting scattered radiation formed by interference between plural predetermined diffraction orders, wherein the predetermined diffraction orders are generated by diffraction of the measurement radiation from the first target structure and are subsequently diffracted from the second target structure; and calculating a characteristic of the lithographic process using the detected scattered radiation formed by the interference between the predetermined diffraction orders.

According to an alternative aspect, there is provided a substrate comprising a target formed by a lithographic process, the target comprising a layered structure having a first target structure in a first layer and a second target structure in a second layer, wherein the first target structure and the second target structure are configured to allow detection of radiation scattered from the target when the target is illuminated with measurement radiation, the detected scattered radiation being formed by interference between plural predetermined diffraction orders, wherein the predetermined diffraction orders are generated by diffraction of the measurement radiation from the first target structure and are subsequently diffracted from the second target structure.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying drawings in which:

FIGS. 3(a)-3(d) comprise 3(a) a schematic diagram of a dark field scatterometer for use in measuring targets using a first pair of illumination apertures, 3(b) a detail of diffraction spectrum of a target grating for a given direction of illumination 3(c) a second pair of illumination apertures providing further illumination modes in using the scatterometer for diffraction based overlay measurements and 3(d) a third pair of illumination apertures combining the first and second pair of apertures;

FIG. 4 depicts a known form of multiple grating target and an outline of a measurement spot on a substrate;

FIG. 5 depicts an image of the target of FIG. 4 obtained in the scatterometer of FIG. 3;

FIGS. 17(a) and 17(b) respectively depict a frequency spectrum and phase spectrum of the fringe patterns of FIG. 16;

FIG. 18 is a plot of measurements of phase for different wavelengths of measurement radiation at two different overlay values;

FIG. 19 is a plot of measurements of phase for different target thicknesses (layer thickness) at five different overlay values;

FIGS. 20(a) and 20(b) are top views respectively of a further example second target structure and a further example first target structure;

DETAILED DESCRIPTION OF EXEMPLARY EMBODIMENTS

Before describing embodiments of the invention in detail, it is instructive to present an example environment in which embodiments of the present invention may be implemented.

Figure 1:
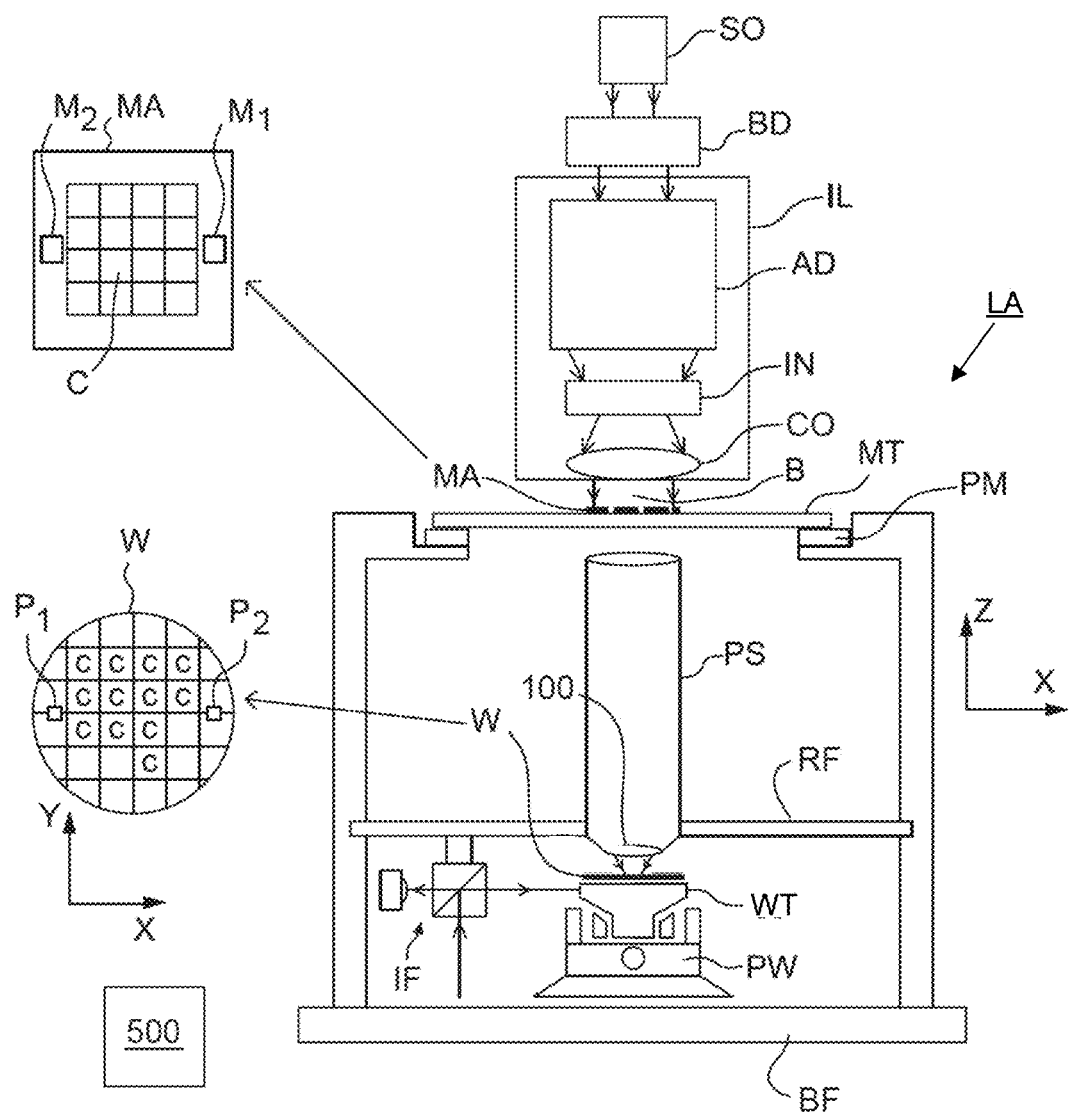
FIG. 1 depicts a lithographic apparatus according to an embodiment of the invention.

FIG. 1 schematically depicts a lithographic apparatus LA. The apparatus includes an illumination optical system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection optical system (e.g., a refractive projection lens system) PS configured to project a pattern imparted to the radiation beam B by patterning device MA onto a target portion C (e.g., including one or more dies) of the substrate W.

The illumination optical system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection optical system PS, which focuses the beam onto a target portion C of the substrate W, thereby projecting an image of the pattern on the target portion C. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. The alignment system, which detects the alignment markers is described further below.

The depicted apparatus can be used in a variety of modes, including for example a step mode or a scan mode. The construction and operation of lithographic apparatus is well known to those skilled in the art and need not be described further for an understanding of the present invention.

Figure 2:
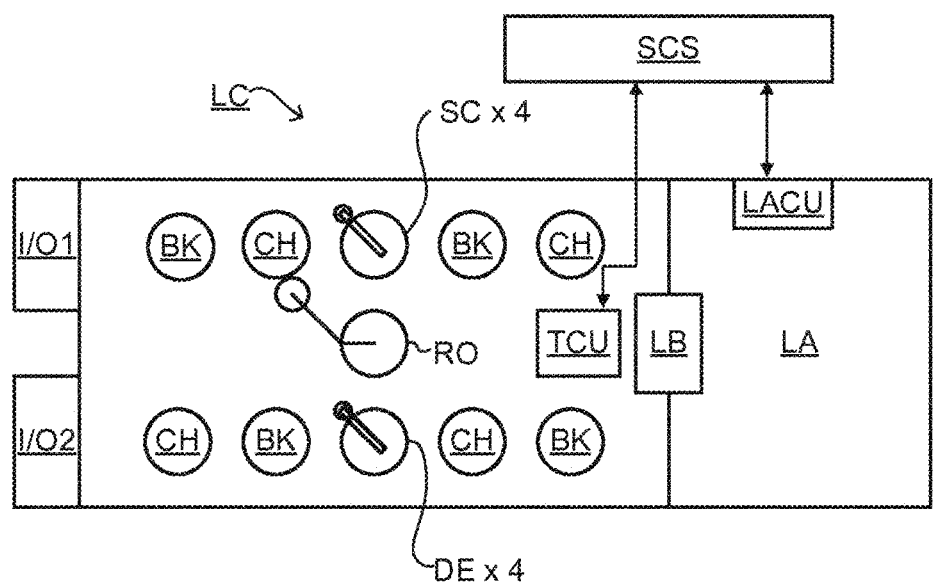
FIG. 2 depicts a lithographic cell or cluster according to an embodiment of the invention.

As shown in FIG. 2, the lithographic apparatus LA forms part of a lithographic system, referred to as a lithographic cell LC or a lithocell or cluster. The lithographic cell LC may also include apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

A metrology apparatus is shown in FIG. 3(a). A target T and diffracted rays of measurement radiation used to illuminate the target are illustrated in more detail in FIG. 3(b). The metrology apparatus illustrated is of a type known as a dark field metrology apparatus. The metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 (e.g., a xenon lamp) is directed onto substrate W via a beam splitter 15 by an optical system comprising lenses 12, 14 and objective lens 16. These lenses are arranged in a double sequence of a 4F arrangement. A different lens arrangement can be used, provided that it still provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

As shown in FIG. 3(b), target T is placed with substrate W normal to the optical axis O of objective lens 16. The substrate W may be supported by a support (not shown). A ray of measurement radiation I impinging on target T from an angle off the axis O gives rise to a zeroth order ray (solid line O) and two first order rays (dot-chain line +1 and double dot-chain line −1). It should be remembered that with an overfilled small target, these rays are just one of many parallel rays covering the area of the substrate including metrology target T and other features. Since the aperture in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches of the targets and the illumination angles can be designed or adjusted so that the first order rays entering the objective lens are closely aligned with the central optical axis. The rays illustrated in FIGS. 3(a) and 3(b) are shown somewhat off axis purely to enable them to be more easily distinguished in the diagram.

At least the 0 and +1 orders diffracted by the target T on substrate W are collected by objective lens 16 and directed back through beam splitter 15. Returning to FIG. 3(a), both the first and second illumination modes are illustrated, by designating diametrically opposite apertures labeled as north (N) and south (S). When the incident ray I of measurement radiation is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A second beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for many measurement purposes such as reconstruction.

In the second measurement branch, optical system 20, 22 forms an image of the target T on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to processor PU which processes the image, the function of which will depend on the particular type of measurements being performed. Note that the term 'image' is used here in a broad sense. An image of the grating lines as such will not be formed, if only one of the −1 and +1 orders is present.

The particular forms of aperture plate 13 and field stop 21 shown in FIG. 3 are purely examples. In another embodiment of the invention, on-axis illumination of the targets is used and an aperture stop with an off-axis aperture is used to pass substantially only one first order of diffracted light to the sensor. In yet other embodiments, 2nd, 3rd and higher order beams (not shown in FIG. 3) can be used in measurements, instead of or in addition to the first order beams.

In order to make the measurement radiation adaptable to these different types of measurement, the aperture plate 13 may comprise a number of aperture patterns formed around a disc, which rotates to bring a desired pattern into place. Note that aperture plate 13N or 13S can only be used to measure gratings oriented in one direction (X or Y depending on the set-up). For measurement of an orthogonal grating, rotation of the target through 90° and 270° might be implemented. Different aperture plates are shown in FIGS. 3(c) and (d). The use of these, and numerous other variations and applications of the apparatus are described in prior published applications, mentioned above.

FIG. 4 depicts an overlay target or composite overlay target formed on a substrate according to known practice. The overlay target in this example comprises four sub-overlay targets (e.g., gratings) 32 to 35 positioned closely together so that they will all be within a measurement spot 31 formed by the metrology radiation illumination beam of the metrology apparatus. The four sub-overlay targets thus are all simultaneously illuminated and simultaneously imaged on sensors 19 and 23. In an example dedicated to measurement of overlay, gratings 32 to 35 are themselves composite gratings formed by overlying gratings that are patterned in different layers of the semi-conductor device formed on substrate W. Gratings 32 to 35 may have differently biased overlay offsets in order to facilitate measurement of overlay between the layers in which the different parts of the composite gratings are formed. The meaning of overlay bias will be explained below with reference to FIG. 7. Gratings 32 to 35 may also differ in their orientation, as shown, so as to diffract incoming radiation in X and Y directions. In one example, gratings 32 and 34 are X-direction gratings with offsets +d, −d, respectively. Gratings 33 and 35 are Y-direction gratings with offsets +d and −d respectively. Separate images of these gratings can be identified in the image captured by sensor 23. This is only one example of an overlay target. An overlay target may comprise more or fewer than 4 gratings, or only a single grating.

FIG. 5 shows an example of an image that may be formed on and detected by the sensor 23, using the overlay target of FIG. 4 in the apparatus of FIG. 3, using the aperture plates 13NW or 13SE from FIG. 3(d). While the pupil plane image sensor 19 cannot resolve the different individual gratings 32 to 35, the image sensor 23 can do so. The dark rectangle represents the field of the image on the sensor, within which the illuminated spot 31 on the substrate is imaged into a corresponding circular area 41. Within this, rectangular areas 42-45 represent the images of the small overlay target gratings 32 to 35. If the overlay targets are located in product areas, product features may also be visible in the periphery of this image field. Image processor and controller PU processes these images using pattern recognition to identify the separate images 42 to 45 of gratings 32 to 35. In this way, the images do not have to be aligned very precisely at a specific location within the sensor frame, which greatly improves throughput of the measuring apparatus as a whole.

Once the separate images of the overlay targets have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an important example of such a parameter.

Figure 6:
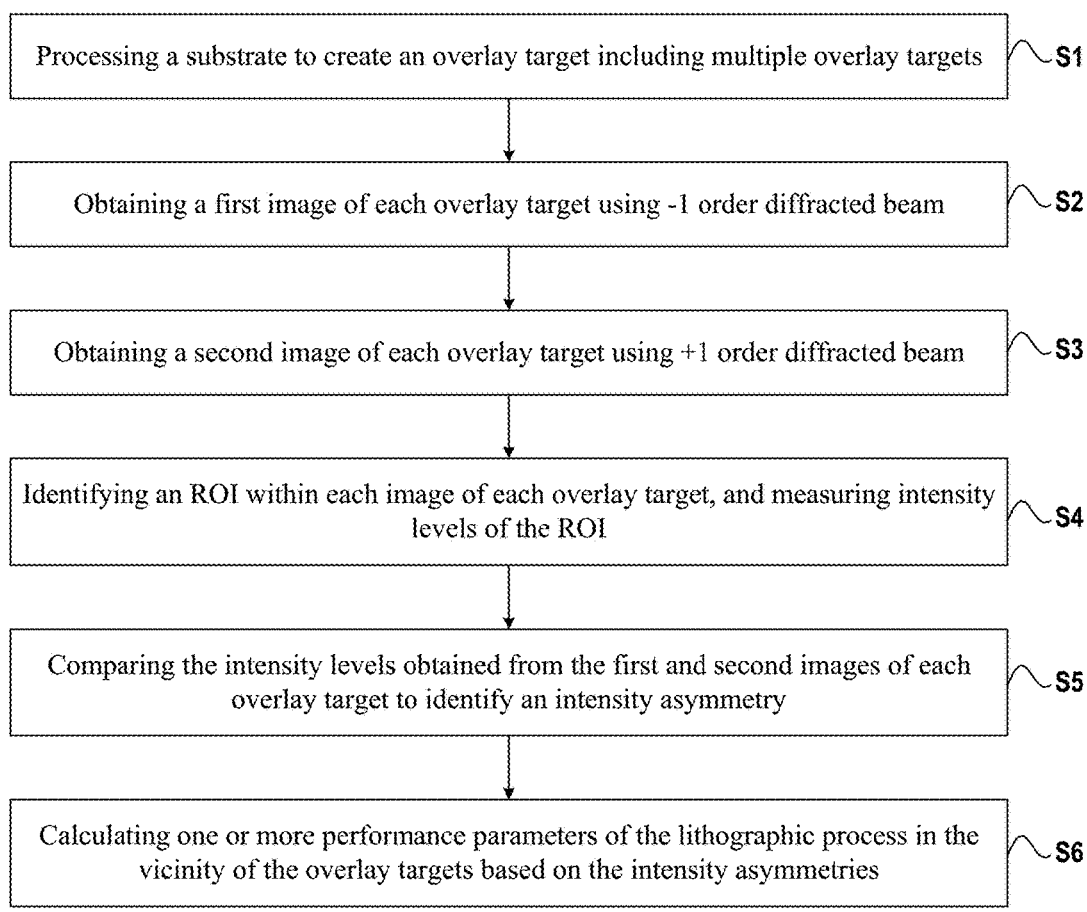
FIG. 6 is a flowchart showing the steps of an overlay measurement method using the scatterometer of FIG. 3 and adaptable to form embodiments of the present invention.

FIG. 6 illustrates how, using for example the method described in application WO 2011/012624, overlay error (i.e., undesired and unintentional overlay misalignment) between the two layers containing the component overlay targets 32 to 35 is measured. Such a method may be referred to as micro diffraction based overlay (µDBO). This measurement is done through overlay target asymmetry, as revealed by comparing their intensities in the +1 order and −1 order dark field images (the intensities of other corresponding higher orders can be compared, e.g. +2 and −2 orders) to obtain a measure of the intensity asymmetry. At step S1, the substrate, for example a semiconductor wafer, is processed through a lithographic apparatus, such as the lithographic cell of FIG. 2, one or more times, to create an overlay target including the gratings 32-35. At S2, using the metrology apparatus of FIG. 3 for example, an image of the overlay targets 32 to 35 is obtained using only one of the first order diffracted beams (say −1). At step S3, whether by changing the illumination mode, or changing the imaging mode, or by rotating substrate W by 180° in the field of view of the metrology apparatus, a second image of the overlay targets using the other first order diffracted beam (+1) can be obtained. Consequently the +1 diffracted radiation is captured in the second image.

Note that, by including only half of the first order diffracted radiation in each image, the 'images' referred to here are not conventional dark field microscopy images. The individual overlay target lines of the overlay targets will not be resolved. Each overlay target will be represented simply by an area of a certain intensity level. In step S4, a region of interest (ROI) is identified within the image of each component overlay target, from which intensity levels will be measured.

Having identified the ROI for each individual overlay target and measured its intensity, the asymmetry of the overlay target, and hence overlay error, can then be determined. This is done (e.g., by the processor PU) in step S5 comparing the intensity values obtained for +1 and −1 orders for each overlay target 32-35 to identify their intensity asymmetry, e.g., any difference in their intensity. The term "difference" is not intended to refer only to subtraction. Differences may be calculated in ratio form. In step S6 the measured intensity asymmetries for a number of overlay targets are used, together with knowledge of any known imposed overlay biases of those overlay targets, to calculate one or more performance parameters of the lithographic process in the vicinity of the overlay target T. In the applications described herein, measurements using two or more different measurement recipes will be included. A performance parameter of great interest is overlay.

Figure 7:
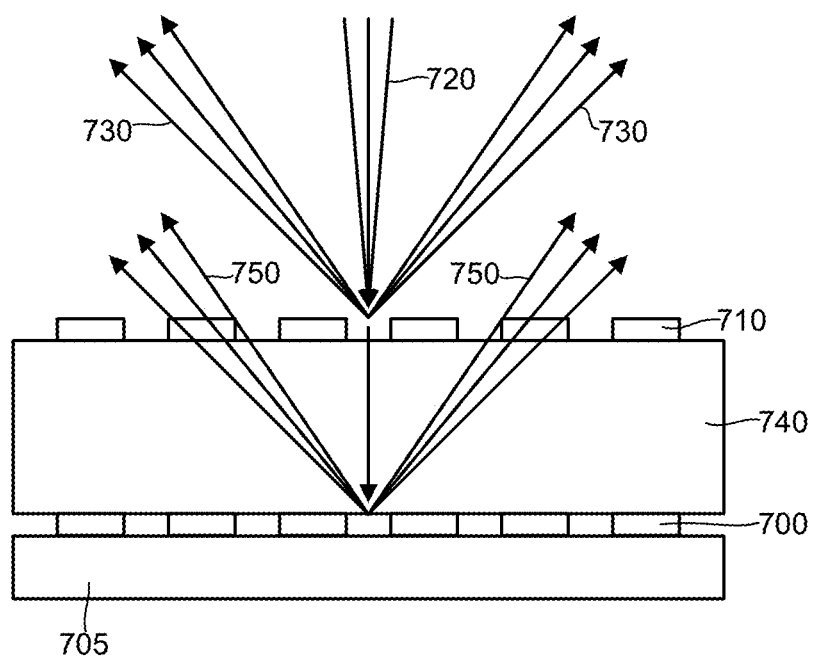
FIG. 7 illustrates some of the main diffraction modes resultant from diffraction by an overlay target in a known manner.

FIG. 7 illustrates a typical diffraction configuration of an overlay target comprising overlapping periodic structures. The overlapping periodic structures comprise a first periodic structure (or first grating) and a second periodic structure (or second grating). In the specific example shown, there is a first (lower) grating 700 in a first layer and a second (upper) grating 710 in a second layer, all formed on a substrate 705. Between the first grating 700 and second grating 710 is layer material 740, which (in this schematic example) may include the material that the second layer structures will be etched into. Measurement radiation 720 is incident on the second grating 710, resulting in diffraction forming non-zero (e.g., first) diffraction orders 730. In addition, some of the measurement radiation 720 (the zeroth order) passes through second grating 710 and layer material 740 to be incident on the first grating 700, where again there is diffraction forming non-zero (e.g., first) diffraction orders 750. The non-zero diffraction orders 730 from the second grating 710 and non-zero diffraction orders 750 from the first grating 700 eventually interfere (e.g., in the far field) to form an overlay signal which can be captured by a sensor (e.g., sensor 19 or sensor 23 of the apparatus depicted in FIG. 3(a)). Note that this diagram is provided only to illustrate the relevant principle of generating an overlay signal and, for simplicity, does not show all the diffraction modes (e.g., the transmissive diffraction modes are not shown). As has already been described, there may be a deliberate offset (not shown) between the first grating 700 and second grating 710.

A metrology target design platform, such as D4C, may be used in designing the metrology (overlay) targets. D4C enables a user to be able to perform all required steps to design metrology targets without intervention from the creator of the D4C program. Appropriate graphic user interfaces (GUI) are made available to set up, execute, review and use the features of the D4C program. Usually, no special interface with the fabrication tools is needed, because the metrology target design is mostly confined in the simulation domain rather than in the actual device manufacturing domain.

Conventional target design tools, such as multi-physics 3-D modeling software, usually "draw" or "build" a geometric structure using area or volume elements which are purely graphical. Those graphical elements are assigned multi-physics parametric characteristics. The fundamental difference of the D4C method with the conventional method is that the lithography process itself drives the rendering of the 3D structure of the metrology targets, so the designers do not have to build the model element-by-element.

Figure 8A:
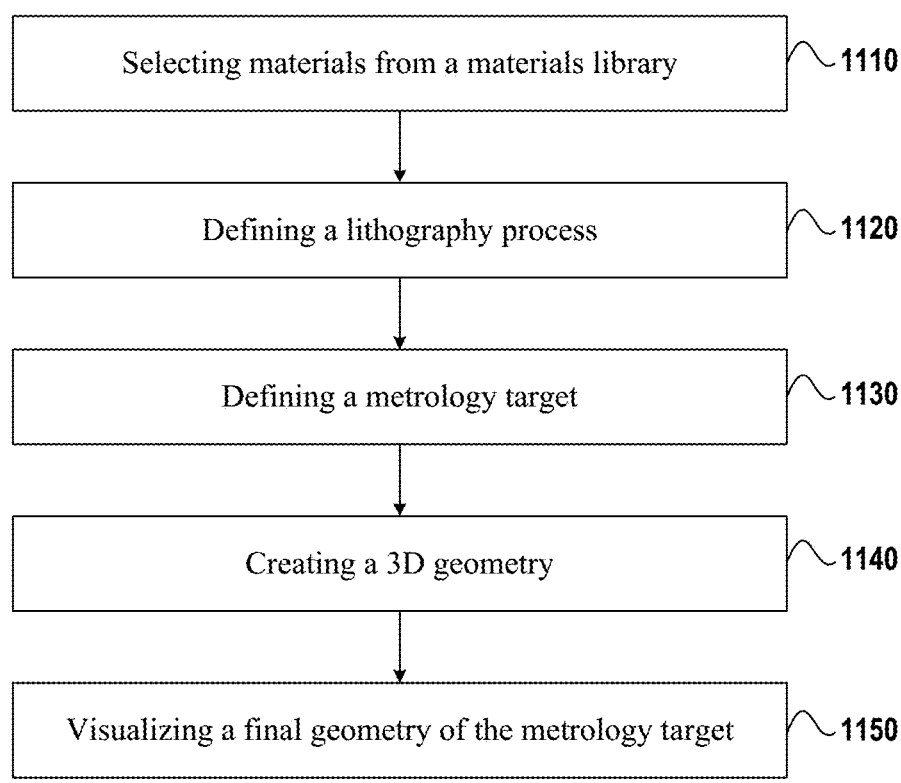
FIGS. 8(a)-8(c) comprise flowcharts of different aspects of an exemplary target design method usable in designing targets disclosed herein.

FIG. 8(a) shows a flowchart that lists the main stages of the D4C method. In stage 1110, the materials to be used in the lithography process are selected. The materials may be selected from a materials library interfaced with D4C through an appropriate GUI. In stage 1120, a lithography process is defined by entering each of the process steps, and building a computer simulation model for the entire process sequence. In stage 1130, a metrology target is defined, i.e. dimensions and other characteristics of various features included in the target are entered into the D4C program. For example, if a grating is included in a structure, then the number of grating elements, width of individual grating elements, spacing between two grating elements etc. have to be defined. In stage 1140, the 3D geometry is created. This step also takes into account if there is any information relevant to a multi-layer target design, for example, the relative shifts between different layers. This feature enables multi-layer target design. In stage 1150, the final geometry of the designed target is visualized. As will be explained in greater detail below, not only the final design is visualized, but as the designer applies various steps of the lithography process, he/she can visualize how the 3D geometry is being formed and changed because of process-induced effects. For example, the 3D geometry after resist patterning is different from the 3D geometry after resist removal and etching.

Figure 8B:
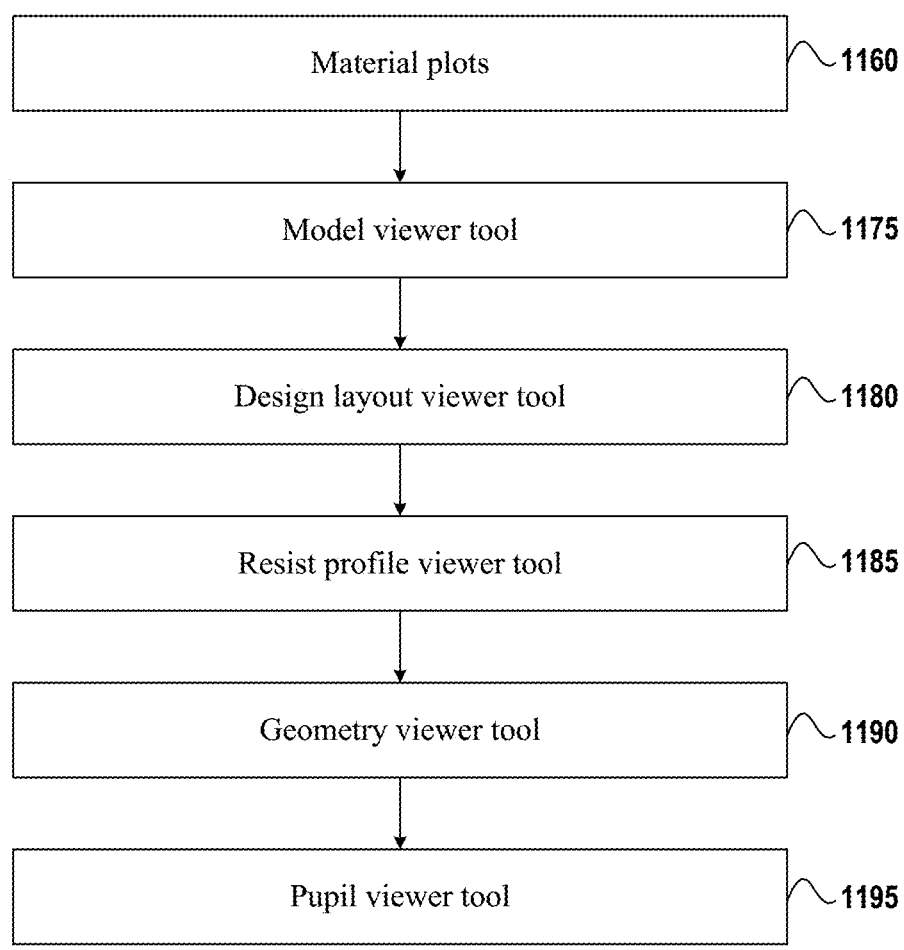

An important aspect of the present disclosure is that the target designer is enabled to visualize the stages of the method to facilitate their perception and control during modeling and simulation. Different visualization tools, referred to as "viewers," are built into the D4C software. For example, as shown in FIG. 8(b), a designer can view material plots 1160 (and may also get a run time estimation plot) depending on the defined lithography process and target. Once the lithography model is created, the designer can view the model parameters through model viewer tool 1175. Design layout viewer tool 1180 may be used to view the design layout (e.g., visual rendering of the GDS file). Resist profile viewer tool 1185 may be used to view pattern profiles in a resist. Geometry viewer tool 1190 may be used to view 3D structures on a wafer. A pupil viewer tool 1195 may be used to view simulated response on a metrology tool. Persons skilled in the art would understand that these viewing tools are available to enhance the understanding of the designer during design and simulation. One or more of these tools may not be present in some embodiments of D4C software, and additional viewing tools may be there in some other embodiments.

D4C enables designers to design thousands or even millions of designs. Not all of these designs will generate a required overlay signal. To determine one or a subset of such target designs which generate overlay signals, the D4C method allows many designs to be evaluated and visualized. Therefore it is possible to identify which targets generate the required overly signals (and which of these provide the best overlay response, and/or are most robust to process variation etc.).

Figure 8C:
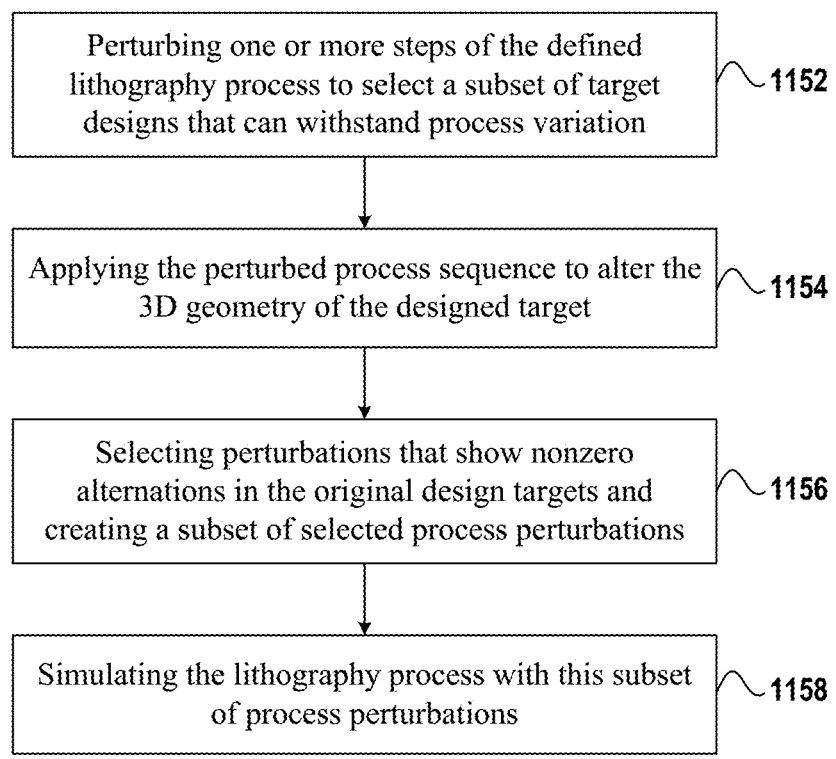
Figure 9:
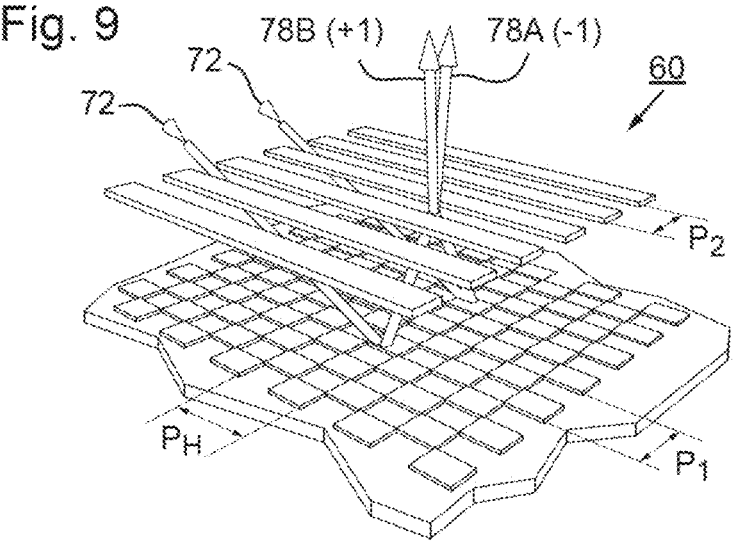
FIG. 9 is a perspective view showing trajectories of example rays through an exemplary target.
Figure 10:
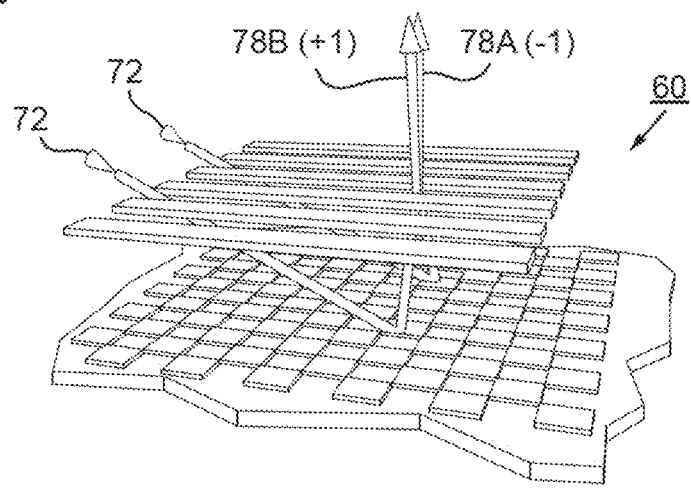
FIG. 10 is a perspective view of the arrangement of FIG. 9 from a different angle.
Figure 11:
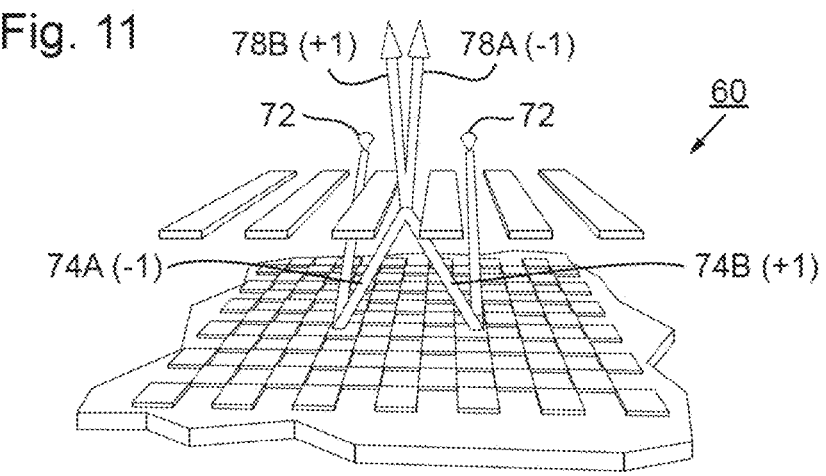
FIG. 11 is a perspective view of the arrangement of FIG. 9 from a further different angle.

FIG. 8(c) shows a flow chart that illustrates how the D4C process increases efficiency in the overall simulation process by reducing the number of metrology targets selected for the actual simulation of the lithography process. As mentioned before, D4C enables designers to design thousands or even millions of designs. Not all of these designs may be robust against variations in the process steps. To select a subset of target designs that can withstand process variation, a lithographer may intentionally perturb one or more steps of the defined lithography process, as shown in block 1152. The introduction of the perturbation alters the entire process sequence with respect to how it was originally defined. Therefore, applying the perturbed process sequence (block 1154) alters the 3D geometry of the designed target too. A lithographer only selects the perturbations that show non-zero alternations in the original design targets and creates a subset of selected process perturbations (block 1156). The lithography process is then simulated with this subset of process perturbations (block 1158). Embodiments described below relate to a method of measurement of a lithographic characteristic using a metrology target and a metrology apparatus.

Optical metrology uses light scattered from a target to provide information about a lithographic process. The measurements are performed in optical instruments such as scatterometers. The information that scatterometers are suitable to measure is, for example, overlay, which is a relative distance between two overlapping gratings, in a plane parallel with the two overlapping gratings.

In a diffraction based overlay measurement, the overlay is extracted from a difference in the light intensity for the first positive and negative first diffracted order. Examples of known scatterometers suitable to measure overlay from diffracted light include those scatterometers described in US2006033921A1, US2010201963A1, US2006066855A1, US2014192338, US2011069292A1, US20110027704A, US20110043791A, US2011102753A1, US20120044470A, US20120123581A, US20130258310A, US20130271740A, WO2016083076A1 and 62/320,780. The contents of all these applications are specifically and entirely incorporated herein by reference.

Further, it is desirable to be able to use a metrology method which provides an optimal and robust result, which in turn leads to accurate overlay measurement.

One of the problems faced by metrology applications for measuring overlay is intensity perturbations that disrupt the balance in intensities diffracted from the two overlapping gratings. Further, in current measuring methods, there are few options to distinguish between intensity variations resulting from overlay and intensity variations resulting from changes in thickness, or wavelength of scattered light. Another source of perturbations arises due to the finiteness of the target, which is manifested in strong signals, such as the edge effects. Furthermore, aberrations of the imaging optics are also a source of intensity perturbations. In the currently known methods of measuring overlay with scatterometry, the overlay sensitivity of the signal is sensitive to layer thickness variations. This is also a challenge that is solved with the embodiment disclosed in this patent application.

It is an object of embodiments disclosed herein to provide a method of accurate and robust measurement of a lithographic characteristic such as overlay. Further, it is an object of embodiments disclosed herein to provide a method of accurate and robust measurement of a lithographic characteristic such as overlay, wherein the measured overlay is independent of the thickness of the stack, thickness such as the distance between the two overlapping gratings. Furthermore, it is an object of embodiments disclosed herein to provide a method of accurate and robust measurement of a lithographic characteristic such as overlay, wherein the measured overlay is independent of the wavelength of the light used to illuminate the metrology target.

To address the above mentioned drawbacks, a target 60 comprising two overlapping gratings is proposed, such as the target 60 of FIGS. 9-12. The target 60 in this example comprises a top grating (an example of a second target structure 92 as referred to below) formed by lines with a pitch $P_2$ and a chessboard (also referred to as checkerboard) grating (an example of a first target structure 91 as referred to below) with a pitch $P_1$ in a direction parallel with the pitch of top grating $P_2$ and pitch $P_H$ in a direction perpendicular to the pitches $P_2$ and $P_1$. When illuminated with light in the visible or infrared or near infrared or ultraviolet or EUV spectrum, the rays follow the paths as depicted in FIGS. 9-12. Normal incidence light (when viewed as in FIGS. 11 and 12) will be diffracted by the bottom grating (first target structure 91) and the resulting diffracted orders +1 and −1 will be diffracted or scattered by the top grating (second target structure 92). The two rays (78A,78B) diffracted by the top grating, having an angle between them of 2*$\theta_2$, are interfering and forming a fringe pattern. The fringe pattern will be detected by a light intensity sensor, such as a camera or photodiode (or plurality of photodiodes) and will form an image having a periodic oscillating pattern. The fringe period, $P_f$, is a function only of the pitches $P_1$ and $P_2$. The angles $\theta_1$ and $\theta_2$ and the period of the fringes $P_f$ are given in below equations, wherein m is an integer.

$$\theta_1 = \operatorname{asin}\left(\frac{m\lambda}{P_1}\right) \qquad \text{equation 1}$$

$$\theta_2 = \operatorname{asin}\left(\frac{m\lambda}{P_2} - \sin\theta_1\right) \qquad \text{equation 2}$$

$$P_f = \frac{\lambda}{2\sin\theta_2} = \frac{P_1 P_2}{2|P_2 - P_1|} \qquad \text{equation 3}$$

Figure 13:
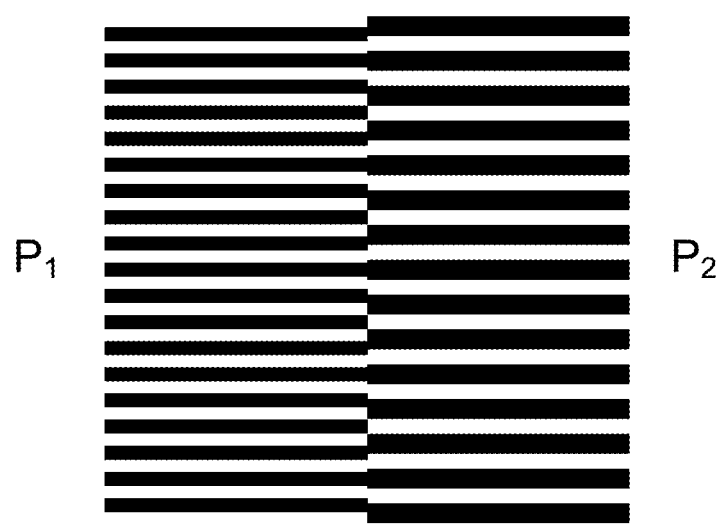
FIG. 13 is a top view of an example second target structure in a target.
Figure 14:
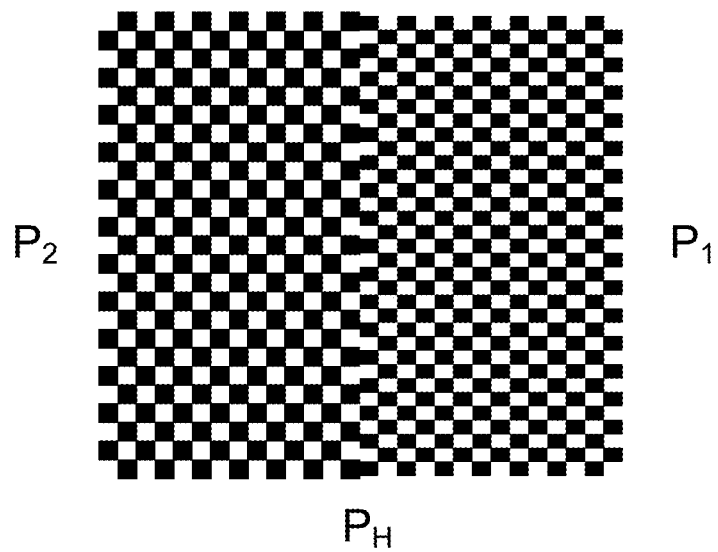
FIG. 14 is a top view of an example first target structure in the target of FIG. 13.
Figure 15:
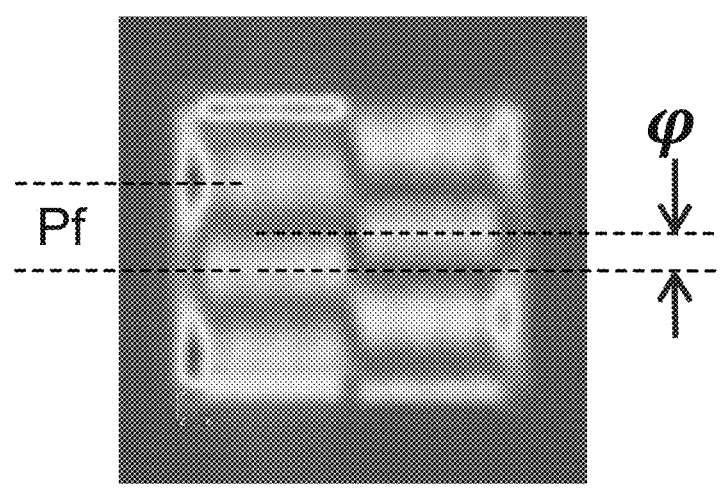
FIG. 15 depicts detected fringe patterns formed from two pairs of overlapping target sub-structures.
Figure 16:
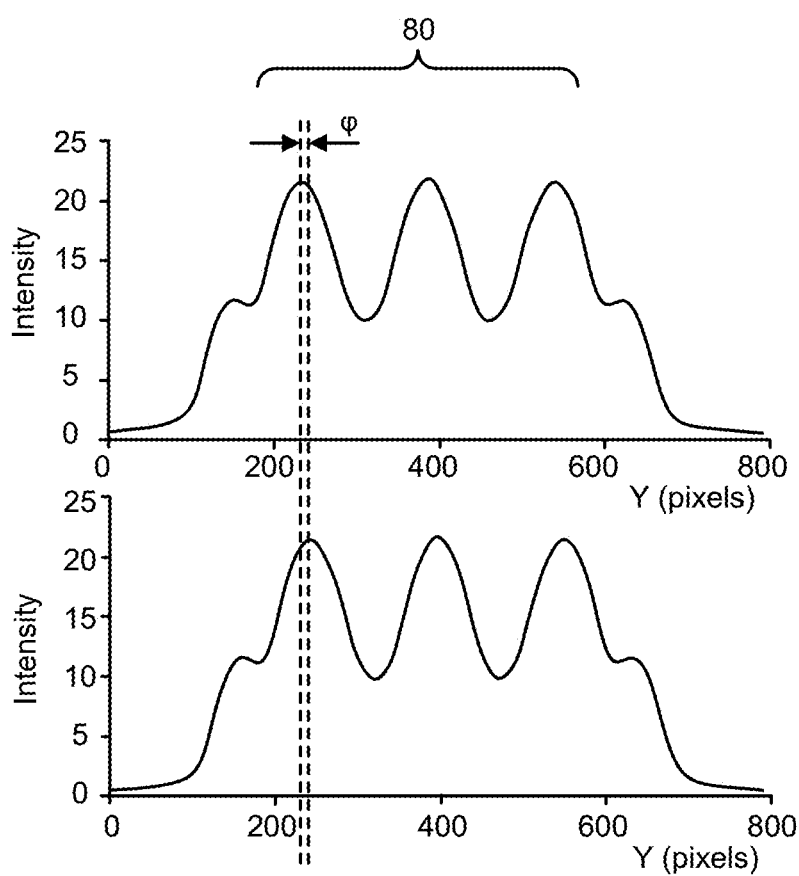
FIG. 16 shows plots of signal intensity (vertical axis) against position (horizontal axis) for fringe patterns in a region of interest.

One example of a preferred target is shown in FIGS. 13 and 14. FIG. 13 depicts an example top grating. FIG. 14 depicts an example bottom grating. The fringe pattern from the target of FIGS. 13 and 14 is shown in FIG. 15. The overlay (the relative shift between the top and bottom grating) is extracted from the shift in the periodic fringe pattern. With known signal processing techniques, the phase $\varphi$ of the periodic signal is extracted, the periodic signal having a frequency equal to the fringe frequency, determined by $P_1$ and $P_2$, as shown in equation 3. Steps in an example signal processing procedure are shown in FIGS. 16 and 17. FIG. 16 shows plots of signal intensity (vertical axis) against position (horizontal axis) for fringe patterns in a region of interest 80 arising from two adjacent pairs of overlapping gratings. A shift in the periodic fringe pattern due to overlay error provides a corresponding phase shift $\varphi$. The phase shift $\varphi$ can be determined from a spatial Fourier analysis of the fringe patterns as shown in FIG. 17. FIG. 17(a) depicts a frequency spectrum of the fringe pattern. FIG. 17(b) depicts a phase spectrum of the fringe pattern. The peak in the frequency spectrum is determined by the fringe period $P_f$. The phase corresponding to the peak (indicated by broken line arrow) provides information about the shift in the fringe pattern, and therefore the overlay error.

A target 60 with a chessboard pattern as a top grating and a line/space pattern as a bottom grating works on a similar principle.

FIGS. 18 and 19 show the dependence of a parameter, such as phase of the periodic signal having a frequency given by the fringe pattern, as a function of wavelength used to illuminate the target 60 (in FIG. 18) and as a function of the stack thickness (in FIG. 19). The overlay, which is directly proportional to the phase according to equation 4, is not dependent on wavelength or stack thickness.

$$\text{Overlay} = \frac{P1 P2}{4\pi(P1 + P2)} \cdot \varphi \qquad \text{equation 4}$$

An alternative design according to an embodiment is shown in FIG. 20, in which FIG. 20(a) depicts a top grating and FIG. 20(b) depicts a bottom grating. A single target is provided with two-dimensional gratings on both top and bottom layers. The top target consists of a 2D grating with pitch $P_1$ (e.g., 500 nm) in both X and Y directions. The bottom target is a checkerboard with pitch $P_2$ (e.g., 450 nm) in both X and Y. In this case $P_H = P_2$. Fiducials consisting of interference fringes would surround the target shown, or placed adjacent, using reversed $P_1$ and $P_2$ on top and bottom. Fixed, periodically-segmented diffraction gratings can also be used for the phase fiducials.

The illumination direction would determine which overlay sensitivity is displayed currently: for X overlay measurement the target would be illuminated predominantly from the Y direction; for Y overlay measurement the target would be illuminated predominantly from the X direction. A different set of interference fringes would be produced depending on the illumination direction and the XY overlay condition.

An advantage to this target design is that it reduces target footprint area by not having duplicated X and Y targets. Another advantage is that the full grating area can be used for measurement in a particular direction, i.e., the full area will be covered by interference fringes, enhancing design flexibility, overlay sensitivity due to larger fringe displacement magnification, and noise reduction by averaging over a larger set of fringes.

The advantage of the current invention is measurement of overlay signal independent of the wavelength and stack layer thickness. This advantage is based on equal path lengths of the +1 and −1 diffracted orders. Further advantage of the invention is insensitivity to edge effects since the phase shift is orthogonal to the target edge facing the illumination source.

Figure 21:
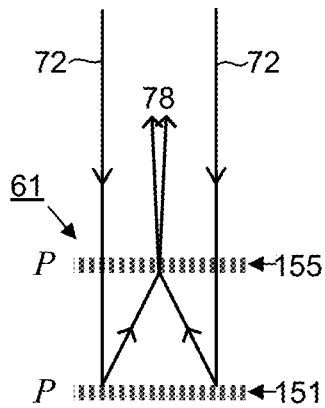
FIG. 21 depicts trajectories of example rays through a target comprising a pair of overlapping target sub-structures having first periodic components with the same pitch.
Figure 22:
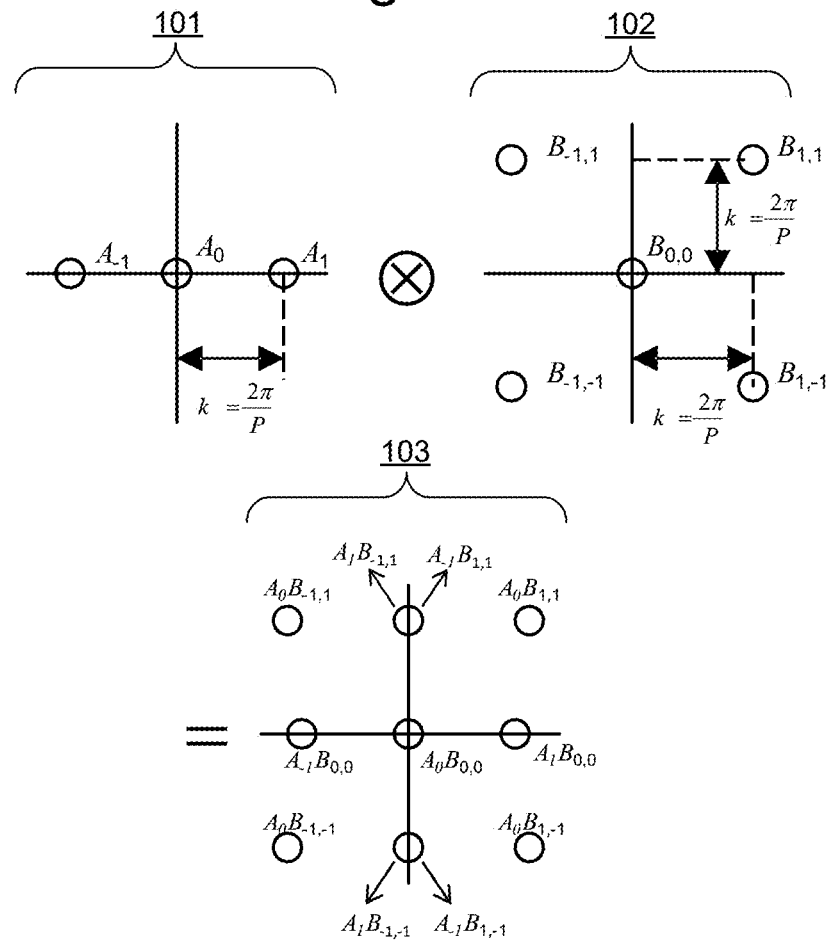
FIG. 22 is a Fourier space representation of diffraction from the overlapping target sub-structures shown in FIG. 21.
Figure 23:
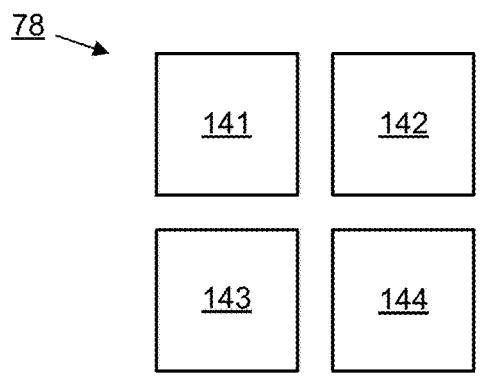
FIG. 23 depicts four intensity sub-regions resulting from scattering from four differently biased pairs of overlapping target sub-structures of the type depicted in FIG. 21.
Figure 24:
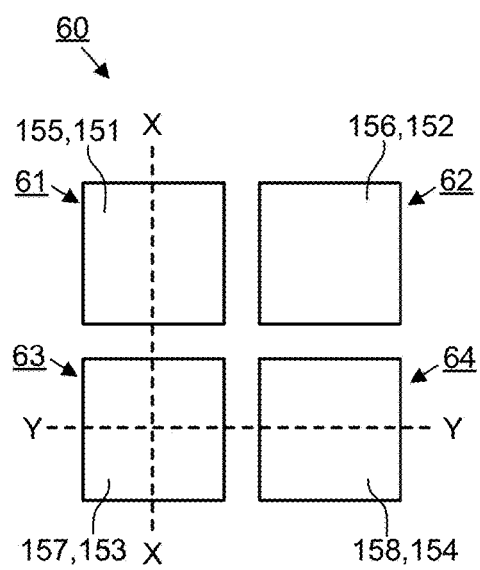
FIG. 24 is a top view of four differently biased pairs of overlapping target sub-structures of the type depicted in FIG. 21.
Figure 25:
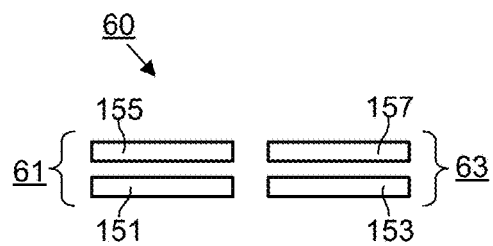
FIG. 25 is a side sectional view perpendicular to plane X-X shown in FIG. 24.
Figure 26:
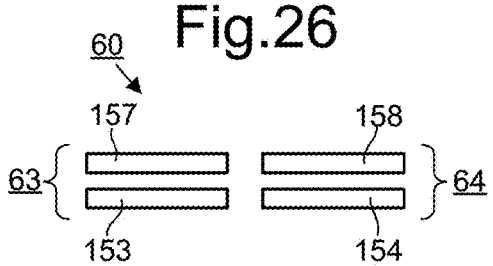
FIG. 26 is a side sectional view perpendicular to plane Y-Y shown in FIG. 24.

FIGS. 21-27 depict yet another embodiment. FIG. 21 shows a target 60 having gratings with equal pitches P illuminated with light (measurement radiation 72). A specific example of such a target 60 is depicted in FIGS. 24-26 and described in detail further below. The image of such a target 60, when illuminated with light in a diffraction based scatterometer, may resemble the squares labeled 141-144 in FIG. 23 (which may be referred to as intensity sub-regions). The squares 141-144 are obtained when illuminating targets having a relative shift (overlay bias) between the top and bottom gratings with, for example, −P/8±d, P/8±d, where P is the equal pitch of the top and bottom grating and d is an arbitrary bias (predetermined constant). Such targets 60 may for example comprise plural pairs 61-64 of overlapping target sub-structures 151-158. Overlay can be extracted from a value proportional to the intensity in each of the images 141-144 or a relation thereof. The intensity of the compound signal 78 in FIG. 23 is given by expressions such as in equations 5 (described in further detail below).

$$I_{0,1} = |A_{-1}B_{1,1} + A_1 B_{-1,1}|^2 = 2A^2 B^2 \left[1 + \cos\left(4\pi \frac{X_s}{P}\right)\right] \quad \text{equations 5}$$

$$I_{0,-1} = |A_{-1}B_{1,-1} + A_1 B_{-1,-1}|^2 = 2A^2 B^2 \left[1 + \cos\left(4\pi \frac{X_s}{P}\right)\right]$$

Figure 27:
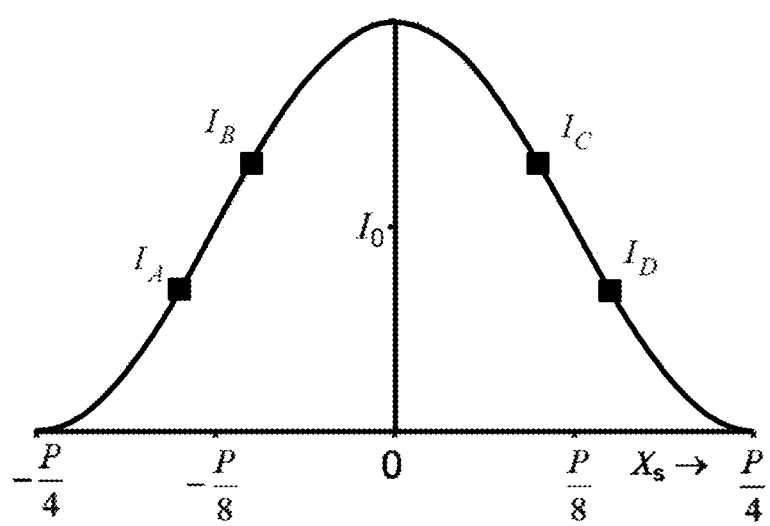
FIG. 27 is a plot of expected intensity variation against overlay offset, showing four expected intensity values corresponding to four differently biased pairs of overlapping target sub-structures of the type depicted in FIG. 21.

The intensity of the component signal 78 varies as a function of the overlay difference $X_s$ between the top and bottom gratings as depicted in FIG. 27. Each of the four intensities shown $I_{A-D}$ corresponds to a different one of the four overlay biases mentioned above (−P/8±d, P/8±d) with zero overlay error. An overlay error will additionally shift the curve to the right or left. The shift can be calculated from the change in the intensities $I_{A-D}$.

In a Fourier analysis of the diffracted rays of light, such as for the example given in FIG. 22 (described in further detail below), interfering light between the first positive and negative diffracted orders will be independent of used wavelength and stack thickness, such as the distance between the gratings. Using different illumination apertures is a method to control the position of the various Fourier components of the diffracted pattern, and therefore increasing the detectability of the signal based only on the diffracted positive and negative order, since such orders are highly sensitive to overlay.

According to an embodiment, a method of measuring a target 60 is provided. The target is formed by a lithographic process. Specific examples of such a method have been discussed above with reference to FIGS. 9-27. The method, and variations on the method, will be described in further detail below.

Figure 12:
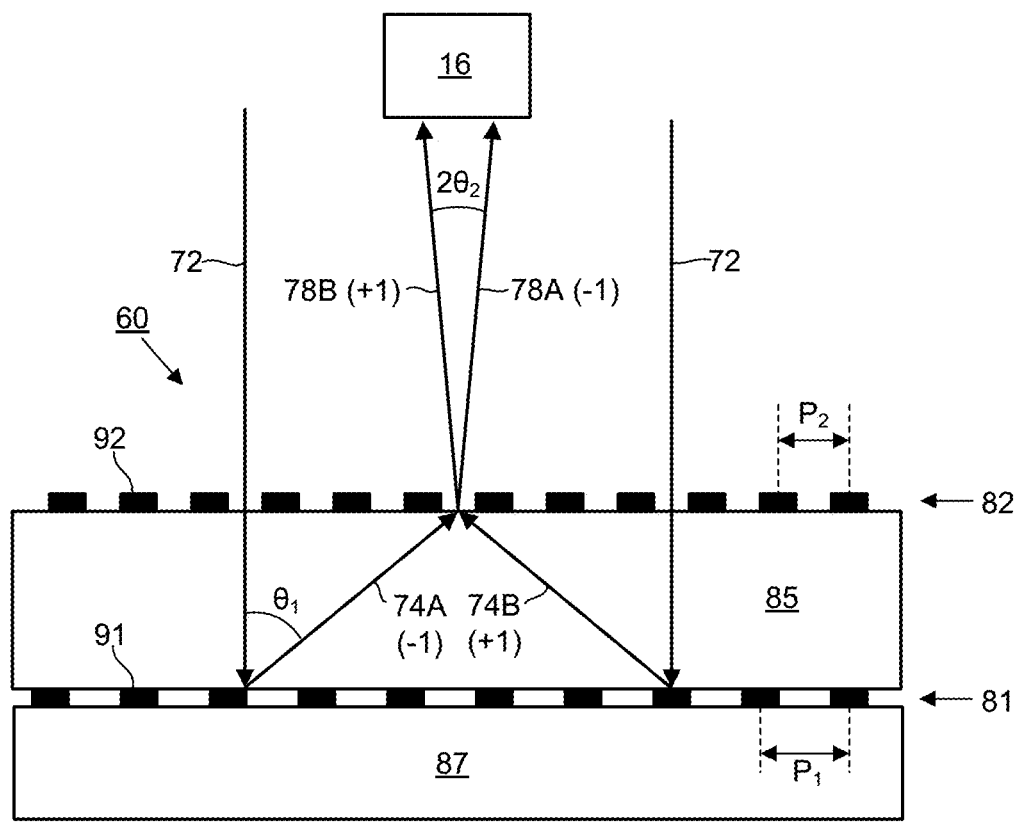
FIG. 12 is a side sectional view of the arrangement of FIG. 9.

As depicted in FIG. 12 for example, the target 60 comprises a layered structure. A first target structure 91 (a periodic structure) is provided in a first layer 81. A second target structure 92 (a periodic structure) is provided in a second layer 82. In between the first target structure 91 and the second target structure 92 is a layer material 85. The layer material 85 may (or may not) contain material that structures forming the second target structure 92 are etched into. The layered structure is formed on a substrate 87.

The target 60 is illuminated with measurement radiation 72. The method comprises detecting scattered radiation formed by interference between plural predetermined (different) diffraction orders 74A,74B. A characteristic of the lithographic process used to form the target, such as overlay error, is calculated using the detected scattered radiation.

The interfering predetermined diffraction orders 74A,74B are generated by diffraction of the measurement radiation 72 from the first target structure 91. In an embodiment the interfering predetermined diffraction orders 74A,74B comprise or consist of two equal and opposite diffraction orders. In the particular example of FIG. 12, the interfering predetermined diffraction orders comprise a −1 diffraction order (negative first order) and a +1 diffraction order (positive first order) (i.e. equal and opposite first diffraction orders). In other embodiments, other predetermined diffraction orders may contribute to the detected scattered radiation formed by interference (e.g. zeroth order or higher orders).

The interfering predetermined diffraction orders 74A,74B initially diverge from the target structure 91 at a relatively large angle θ1. Subsequent diffraction by the second target structure 92 causes the interfering predetermined diffraction orders 74A,74B to be brought closer together (as depicted by rays 78A and 78B, which diverge at a much smaller angle θ$_2$). Ray 78A is a −1 diffraction order generated from ray 74A and ray 78B is a +1 diffraction order generated from ray 74B. The method uses rays 78A and 78B to form an interference pattern (or region of uniform intensity caused by interference) and uses the interference pattern (or region of uniform intensity caused by interference) to measure an overlay error. The detection of the interference between the predetermined diffraction orders is enabled by the subsequent diffraction from the second target structure 92. This subsequent diffraction brings the predetermined diffraction orders close enough together for them to be received efficiently and simultaneously by an objective lens 16 of a detection system and for the interference pattern (or region of uniform intensity caused by interference) to be sensitive to overlay error. Where a metrology apparatus of the type shown in FIG. 3(*a*) is used, for example, the interference pattern may be measured by the second measurement branch.

The path lengths of the interfering predetermined diffraction orders through the layered structure are equal. Intensity variations in the detected scattered radiation caused by path length effects (e.g. greater attenuation for longer path lengths) are thus avoided. The measurement will also be independent of the thickness of the target 60 (e.g. the separation between the first target structure 91 and the second target structure 92, which may also be referred to as the thickness of the stack). The measurement will be effective for thin targets 60 and thick targets 60. As will be described in detail below, the detected interference pattern (or region of uniform intensity caused by interference) is also independent of the wavelength of the radiation. This reduces or avoids errors caused by changes or differences in the spectrum of measurement radiation as it propagates through the target 60.

The detected scattered radiation formed by interference between the predetermined diffraction orders varies as a function of overlay error between the first target structure 91 and the second target structure 92. There are multiple ways in which the first target structure 91 and second target structure 92 may be configured to provide the variation in the detected scattered radiation as a function of overlay error. Specific examples have been described above. Further specific examples will be described below.

In an embodiment, the interfering predetermined diffraction orders 74A,74B are generated by diffraction in reflection from the first target structure 91. The subsequent diffraction of the generated diffraction orders 74A, 74B from the second target structure 92 comprises diffraction in transmission through the second target structure 92. FIG. 12 shows an embodiment of this type. In other embodiments, alternative geometries may be used. For example, in other embodiments the predetermined diffraction orders 74A, 74B are generated by diffraction in transmission through the first target structure 91. Additionally or alternatively, the subsequent diffraction comprises diffraction in reflection from the second target structure 92.

In an embodiment, the interfering predetermined diffraction orders are generated by diffraction in transmission through the first target structure and the subsequent diffraction of the predetermined diffraction orders from the second target structure comprises diffraction in reflection from the second target structure. Such an embodiment could be used to provide rays 78A and 78B similar to those shown in FIG. 12, but the first target structure would in this case need to be above the second target structure instead of below. Thus, in such an embodiment, the target structure labelled 91 in FIG. 12 would correspond to the second target structure and the target structure labelled 92 would correspond to the first target structure. Measurement radiation 72 would diffract firstly from the target structure labelled 92 (rather than passing straight through as in FIG. 12) and then diffract a second time (in reflection) from the target structure labelled 91 (before passing straight through the target structure labelled 92 as rays 78A and 78B).

Thus, the measurement radiation 72 doubly diffracts in either order from an upper target structure and a lower target structure. The double diffraction brings together different diffraction orders to produce characteristic interference (with characteristic intensity and/or with a fringe pattern of characteristic frequency and phase) that is insensitive to wavelength and stack thickness. In practice, the two sequences of diffractions occur simulataneously and reinforce. Diffracted orders that originate from a single diffraction, or from three diffractions, are at significantly different angles and do not contribute to the observed interference (e.g. intensity and/or fringe pattern).

In an embodiment, the target 60 comprises three or more pairs 61-64 of overlapping target sub-structures 151-158. An example of such a target 60 was mentioned briefly above with reference to FIGS. 21-27. The structure of an example target 60 is depicted in FIGS. 24-26. Each pair 61-64 of overlapping target sub-structures 151-158 in such an embodiment comprises a first target sub-structure 151-154. The first target sub-structure 151-154 is provided in the first target structure 91 (i.e. in the first layer 81). Each pair 61-64 of overlapping target sub-structures 151-158 in such an embodiment further comprises a second target sub-structure 155-158. The second target sub-structure 155-158 is provided in the second target structure 92 (i.e. in the second layer 82). In the example of FIGS. 24-26, four pairs are provided. The first pair 61 comprises a first target sub-structure 151 and a second target sub-structure 155. The second pair 62 comprises a first target sub-structure 152 and a second target sub-structure 156. The third pair 63 comprises a first target sub-structure 153 and a second target sub-structure 157. The fourth pair 64 comprises a first target sub-structure 154 and a second target sub-structure 158.

Each of the first target sub-structure 151-154 and the second target sub-structure 155-158 in each pair 61-64 of overlapping target sub-structures 151-158 comprises a first periodic component (e.g. a line grating or a periodic component of a checkerboard pattern) having the same pitch and orientation. In the embodiment of FIGS. 21-27, the first periodic component comprises a grating having a pitch P along at least one direction (e.g. a line grating with pitch P or a checkerboard pattern with pitch P). Each pair 61-64 of overlapping target sub-structures 151-158 is provided with a different overlay bias. Providing the pairs 61-64 of overlapping target sub-structures 151-158 with different overlay biases makes it possible for an overlay error to be obtained with high reliability and/or high accuracy, as described below.

FIG. 22 is a Fourier space representation of diffraction from the pair 61 of overlapping target sub-structures 151, 155 shown in FIG. 21. The skilled person would appreciate that the same principle would apply to each of the other pairs 62-64 of overlapping target sub-structures 152-154,156-158.

Graph 101 represents an expected diffraction pattern (Fourier transform) of the target sub-structure 155. Graph 102 represents an expected diffraction pattern (Fourier transform) of the target sub-structure 151. Graph 103 represents an expected diffraction pattern (Fourier transform) resulting from diffraction from a combined structure formed from a combination of the target sub-structure 155 and target sub-structure 151. The combined structure is formed by superposing (or multiplying) the target sub-structure 155 with the target sub-structure 151. The diffraction pattern of graph 103 can therefore be obtained by convolution of the diffraction pattern of graph 101 with the diffraction pattern of graph 102, as shown in the FIG. 22.

The diffraction pattern of graph 101 comprises a −1, zeroth, and a +1 diffraction order, represented respectively by localized peaks having associated Fourier coefficients $A_{-1}$, $A_0$ and $A_1$. All of the peaks are aligned along the horizontal axis because the target sub-structure 155 in this example consists of a simple line grating (the first periodic component). The only spatial periodicity is therefore represented by the pitch of the line grating, which is in turn represented by the separation along the horizontal axis of the peaks $A_{-1}$ and $A_1$ (equal to 2*k, where k=2π/P).

The diffraction pattern of graph 102 comprises more peaks because the target sub-structure 151 comprises both a first periodic component and a second periodic component. The first periodic component is parallel to the line grating in the target sub-structure 155 and has the same pitch P. The second periodic component is perpendicular to the first periodic component (e.g. a checkerboard pattern). Peaks resulting from diffraction from the combination of the first periodic component and the second periodic component comprise a zeroth order peak with Fourier coefficient $B_{0,0}$ and first order peaks with Fourier coefficients $B_{-1,1}$, $B_{1,1}$, $B_{1,-1}$ and $B_{-1,-1}$. The separation between peaks $B_{-1,1}$ and $B_{1,1}$ and between peaks $B_{1,-1}$ and $B_{-1,-1}$ is determined by the pitch P of the first periodic component. The separation between peaks $B_{-1,1}$ and $B_{-1,-1}$ and between $B_{1,1}$ and $B_{1,-1}$ is determined by the pitch of the second periodic component, which in the particular example shown is also P but could be any other value.

The convolution of the diffraction patterns of graphs 101 and 102 effectively superposes the three peaks $A_{-1}$, $A_0$ and $A_1$ of graph 101 at each of the positions of the peaks $B_{0,0}$, $B_{-1,1}$, $B_{1,1}$, $B_{1,-1}$ and $B_{-1,-1}$ of graph 102. Due to the identical pitch P of the first periodic component in each of the two target sub-structures 151 and 155, first order diffraction peaks in the diffraction pattern of graph 103 are formed from overlapping peaks generated from different predetermined diffraction orders. The localized nature of the overlapping peaks in Fourier space indicates that scattered radiation formed by interference between the predetermined diffraction orders will be output from the target 60 at nominally the same angle (or within a small range of angles). Each of the first order peaks along the vertical axis in graph 103 is formed from overlap of a peak corresponding to +1 diffraction from the target sub-structure 151 followed by −1 diffraction from the target sub-structure 155 ($A_1B_{-1,1}$ or $A_1B_{-,1-1}$) with a peak corresponding to −1 diffraction from the target sub-structure 151 followed by +1 diffraction from the target sub-structure 155 ($A_{-1}B_{1,1}$ or $A_{-1}B_{1,-1}$). The predetermined diffraction orders that interfere with each other are thus defined with respect to diffraction from the first periodic component in the pair 61 (thus, in the present case the predetermined diffraction orders are the +1 and −1 diffraction orders with respect to the first periodic component having the period P in each of the two target sub-structures 151 and 155). The intensities $I_{0,1}$ and $I_{0,-1}$ of scattered radiation produced by the overlapping peaks in graph 103 are given by the expressions provided above in equations 5. It is well known in metrology how to selectively measure scattered radiation corresponding to selected regions in Fourier space, for example by selecting a suitable illumination mode using an aperture plate 13 as described above with reference to FIG. 3. The intensities $I_{0,1}$ and $I_{0,-1}$ can therefore be measured.

Each of the intensities $I_{0,1}$ and $I_{0,-1}$ will vary as a function of the overlay offset between the first periodic components in the overlapping target sub-structures 151-158 of each pair 61-64. An example variation of intensity with overlay offset is depicted in FIG. 27 and mentioned above. The variation is expected to be at least approximately sinusoidal with an average intensity of $I_0$. In an embodiment, an overlay error is detected by measuring a change in the position of the curve to the right or to the left by measuring intensities at different overlay biases.

In an embodiment, the different overlay biases comprise one or more pairs of equal and opposite overlay biases. Such overlay biases provide a symmetric sampling of the intensity variation as a function of overlay offset, which is expected to be less sensitive to the presence of higher harmonics in the signal. In an embodiment, the different overlay biases comprise the following four biases: −P/8−d, P/8+d, −P/8+d and P/8−d, where P is the pitch of the first periodic component and d is a predetermined constant. An example of this type has been discussed above with reference to FIGS. 21-27. As can be seen from FIG. 27, the intensities $I_{A-D}$ resulting from these four overlay biases are nominally symmetrically distributed about the origin. Additionally, by positioning the overlay biases within a limited range either side of the steepest part of the nominal curve (at P/8), all of the intensities $I_{A-D}$ will be nominally positioned at regions having a relatively high steepness. Any change in the position of the curve due to overlay error will therefore result in a relatively rapid change in the measured intensities $I_{A-D}$, thereby favoring high sensitivity.

The four intensities $I_{A-D}$ are related to overlay error OV, in the case where the biases are given by −P/8−d, P/8+d, −P/8+d and P/8−d, by the following equations:

$$I_A = I_0 + K(OV-d)$$

$$I_B = I_0 + K(OV+d)$$

$$I_C = I_0 - K(OV-d)$$

$$I_D = I_0 - K(OV+d)$$

These four equations contain only three unknowns and so can be solved to find OV:

$$OV = d\left[\frac{(I_A - I_C) + (I_B - I_D)}{(I_A - I_C) - (I_B - I_D)}\right]$$

In embodiments of the type discussed above with reference to FIGS. 21-27, the detected scattered radiation formed by interference between the predetermined diffraction orders comprises a plurality of intensity sub-regions 141-144 (as shown in FIG. 23). Each intensity sub-region 141-144 is formed by measurement radiation diffracted from a different respective pair of the three or more pairs 61-64 of target sub-structures 151-158. In the particular example of FIG. 23, four square intensity sub-regions 141-144 are provided by the square array target 60 depicted in FIGS. 24-26. Although each intensity sub-region 141-144 is formed by interference, only a single value of intensity is obtained at any given time. The intensity sub-regions 141-144 do not individually comprise an interference pattern having any interference generated spatial structure (e.g. an interference fringe pattern). This lack of spatial structure is a result of the high degree of overlap in Fourier space of the peaks that are interfering to produce the detected intensity. Detecting a single absolute value of a spatially uniform intensity rather than detecting a pattern having spatial structure is desirable because existing methods of measuring overlay (as described above with reference to FIGS. 3-6) also rely on measurements of a single absolute value of intensity and can therefore be adapted particularly efficiently to perform the present method.

In an alternative embodiment, an interference pattern is formed which does have spatial structure and the spatial structure is used to extract overlay. An example of such a method is described below with reference to FIGS. 28-31.

Figure 30:
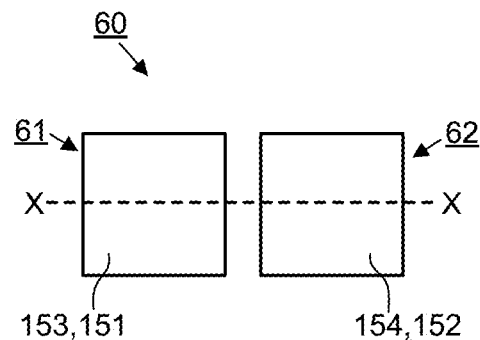
FIG. 30 is a top view of two pairs of overlapping target sub-structures of the type depicted in FIG. 29.
Figure 31:
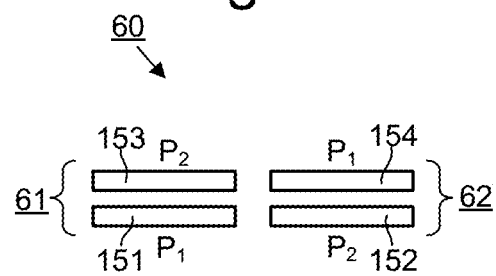
FIG. 31 is a side sectional view perpendicular to plane X-X shown in FIG. 30.

In such a method, a target 60 is provided that comprises at least one pair 61, 62 of overlapping target sub-structures 151-154. An example of such a target 60 is depicted in FIGS. 30 and 31. Each pair 61, 62 of overlapping target sub-structures 151-154 comprises a first target sub-structure 151, 152 in the first target structure 91 (i.e. in the first layer 81) and a second target sub-structure 153, 154 in the second target structure 92 (i.e. in the second layer 82). The first target sub-structure 151, 152 and the second target sub-structure 153, 154 in each pair 61, 62 of overlapping target sub-structures 151-154 comprises a first periodic component having the same orientation and a different pitch $P_1$, $P_2$. As described below, the different pitches $P_1$, $P_2$ provide an interference pattern between different predetermined diffraction orders that has a spatial structure. In an embodiment, the detected scattered radiation formed by interference between the predetermined diffraction orders comprises a fringe pattern formed by each pair 61, 62 of target sub-structures 151-154. In an embodiment, the fringe pattern is such that a variation in overlay error between the first target structure 91 and the second target structure 92 causes a positional shift of fringes in (i.e. a change in phase of) each fringe pattern. Overlay error can thus be obtained by extracting the phase of the fringe pattern.

Figure 28:
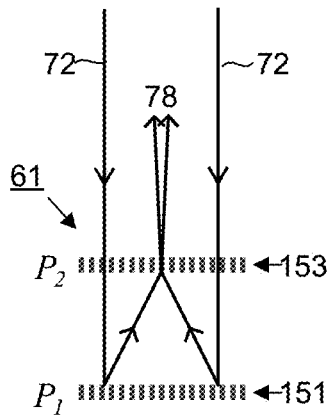
FIG. 28 depicts trajectories of example rays through a target comprising a pair of overlapping target sub-structures having first periodic components with different pitch.
Figure 29:
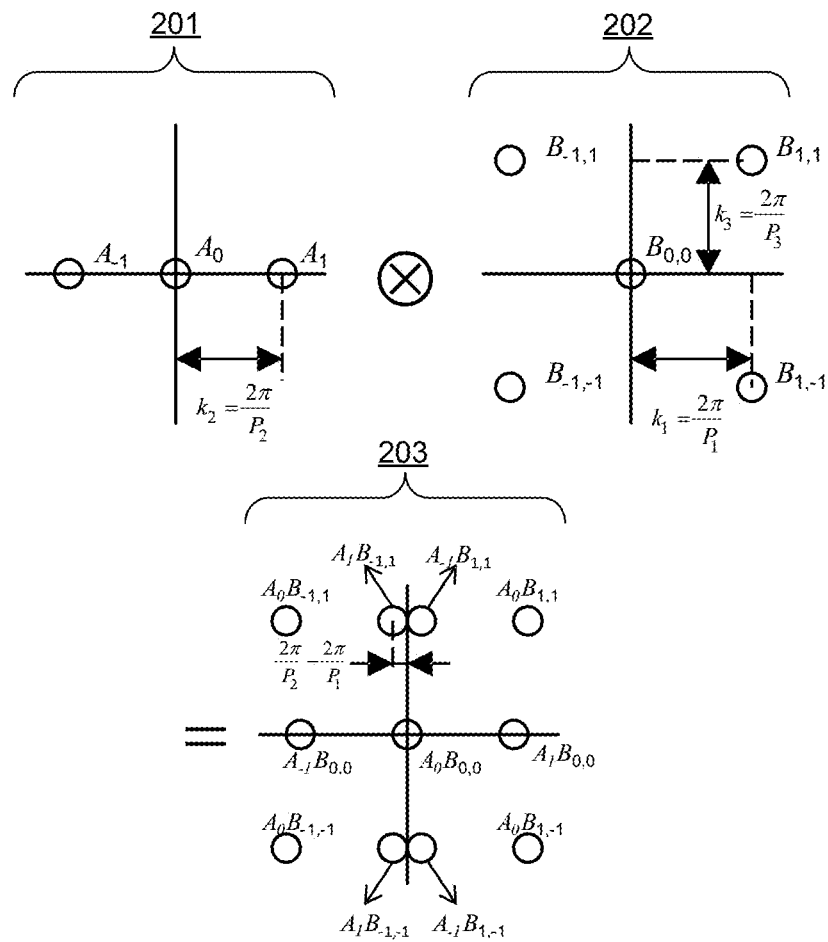
FIG. 29 is a Fourier space representation of diffraction from the overlapping target sub-structures shown in FIG. 28.

FIG. 29 is a Fourier space representation of diffraction from the pair 61 of overlapping target sub-structures 151, 153 shown in FIG. 28. The skilled person would appreciate that the same principle would apply to the other pair 62 of overlapping target sub-structures 152, 154.

The pair 61 of overlapping target sub-structures 151, 153 shown in FIG. 28 is the same as the pair 61 of overlapping target sub-structures 151, 155 shown in FIG. 21 except that the pitch $P_1$ of the lower target sub-structure 151 is different from the pitch $P_2$ of the upper target sub-structure 153. Additionally, the target sub-structure 151 comprises a second periodic component have a pitch $P_3$ (which may be equal to $P_1$ or $P_2$ or any other value).

Graph 201 represents an expected diffraction pattern (Fourier transform) of the target sub-structure 153. Graph 202 represents an expected diffraction pattern (Fourier transform) of the target sub-structure 151. Graph 203 represents an expected diffraction pattern (Fourier transform) resulting from diffraction from a combined structure formed from a combination of the target sub-structure 153 and target sub-structure 151. The combined structure is formed by superposing (or multiplying) the target sub-structure 153 with the target sub-structure 151. The diffraction pattern of graph 203 can therefore be obtained by convolution of the diffraction pattern of graph 201 with the diffraction pattern of graph 202, as shown in the FIG. 29.

The diffraction pattern of graph 201 is the same as the diffraction pattern of graph 101 in FIG. 22 except that the separation between the −1 and +1 peaks is given by $2*k_2$, where $k_2 = 2\pi/P_2$.

The diffraction pattern of graph 202 is the same as the diffraction pattern 102 in FIG. 22 except that the separation between the −1 and +1 peaks along the horizontal direction is given by $2*k_1$, where $k_1=2\pi/P_1$, and the separation between the −1 and +1 peaks along the vertical direction is given by $2*k_3$, where $k_1=2\pi/P_3$.

The convolution of the diffraction patterns of graphs 201 and 202 effectively superposes the three peaks $A_{-1}$, $A_0$ and $A_1$ of graph 201 at each of the positions of the peaks $B_{0,0}$, $B_{-1,1}$, $B_{1,1}$, $B_{1,-1}$ and $B_{-1,-1}$ of graph 202. Due to the different pitches $P_1$ and $P_2$ of the first periodic component in each of the two target sub-structures 151 and 153, a diffraction pattern is formed which comprises two distinct peaks in the region of the overlapping first order peaks (corresponding to the predetermined diffraction orders) in graph 103 of FIG. 22. The distinct peaks are separated from each other, as indicated, by $2\pi/P_2-2\pi/P_1$. The peaks from these predetermined diffraction orders are located close to each other in Fourier space and can therefore be extracted efficiently and used to form an intensity pattern in which the predetermined diffraction orders interfere with each other. Each of the pairs of peaks from the predetermined diffraction orders in graph 203 comprises a peak corresponding to +1 diffraction from the target sub-structure 151 followed by −1 diffraction from the target sub-structure 153 ($A_1$, $B_{-1,1}$ or $A_1 B_{-1,-1}$) and a peak corresponding to −1 diffraction from the target sub-structure 151 followed by +1 diffraction from the target sub-structure 153 ($A_{-1} B_{1,1}$ or $A_{-1} B_{1,-1}$). The predetermined diffraction orders that interfere with each other are thus defined with respect to diffraction from the first periodic component in the pair 61 (in this case the +1 and −1 diffraction orders with respect to diffraction from the first periodic component in the pair 61). The intensities $I_{0,1}$ and $I_{0,-1}$ of each of these pairs of peaks in graph 203 are given by a generalized form of the equations 5, which are labelled equations 6 and given as follows:

$$I_{0,1} = |A_{-1}B_{1,1} + A_1 B_{-1,1}|^2 = \qquad \text{equations 6}$$
$$2A^2B^2\left[1+\cos\left(4\pi\frac{X_s}{P_2}+4\pi\left(\frac{x}{P_2}-\frac{x}{P_1}\right)\right)\right]$$

$$I_{0,-1} = |A_{-1}B_{1,-1} + A_1 B_{-1,-1}|^2 =$$
$$2A^2B^2\left[1+\cos\left(4\pi\frac{X_s}{P_2}+4\pi\left(\frac{x}{P_2}-\frac{x}{P_1}\right)\right)\right]$$

Equations 6 differ from equations 5 in that the intensities $I_{0,1}$ and $I_{0,-1}$ further comprise a spatially periodic term having a pitch (which may also be referred to as a Moiré period) proportional to $$1/2\left|\frac{P_1-P_2}{P_1 P_2}\right|,$$

and a phase proportional to the overlay offset $X_S$. The spatially periodic term defines the pitch and phase of a fringe pattern formed by the intensities $I_{0,1}$ and $I_{0,-1}$. Overlay error will cause a shift in the phase of the fringe pattern. Measurement of the phase can therefore be used to measure overlay error. A sensitivity of the phase to overlay error can varied as desired by appropriate selection of $P_1$ and $P_2$.

Producing an interference pattern having spatial structure (e.g. a fringe pattern) enables filtering in the spatial frequency domain (as depicted in FIG. 17). Contributions to detected radiation intensity that are not relevant to overlay can be removed. Examples of intensity contributors that can be excluded include target edge peaks, asymmetric illumination and scattered light from adjacent devices or other structures. The phase of the interference pattern can therefore be extracted with high accuracy and reliability.

The phase of the fringe pattern advantageously varies linearly with overlay error throughout the $+\pi$ to $-\pi$ phase range. This linear variation facilitates calibration and provides uniform sensitivity.

Figure 32:
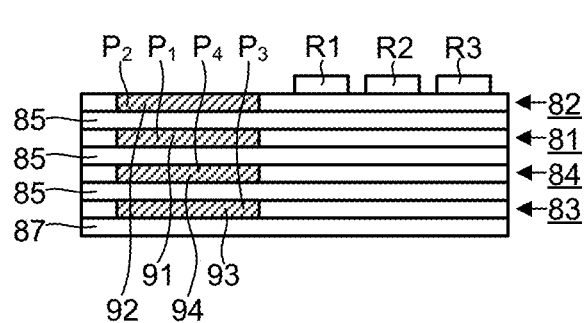
FIG. 32 is a side sectional view of a target comprising four target structures with different pitches in different layers.

In an embodiment, an example of which is depicted in FIG. 32, the target 60 further comprises a reference structure R1 to act as a phase reference. The reference structure R1 provides a radiation pattern having the same periodicity as the fringe pattern. The reference structure R1 is provided in such a way that there is substantially no positional shift of fringes in the radiation pattern from the reference structure R1 as a function of overlay error between the first target structure 91 and the second target structure 92. For example, the reference structure R1 may be formed entirely within a single layer of the target. Thus, a relative shift between the fringe pattern and the radiation pattern from the reference structure R1 can be used to obtain overlay error. In the particular example of FIG. 32, the target 60 comprises four target structures 91-94, but it will be appreciated that the principle can be applied to a target 60 contained only two target structures (as in FIGS. 30 and 31 for example) or any other number of target structures.

An alternative or additional approach to providing a phase reference is to provide a target 60 which produces fringes that move in opposite directions relative to each other as a function of overlay error. An example target 60 of this type is depicted in FIGS. 30 and 31. The target 60 comprises at least a first pair 61 of overlapping target sub-structures 151 and 153, and a second pair 62 of overlapping target sub-structures 152 and 154. In the first pair 61 of overlapping target sub-structures 151 and 153, the first periodic component of the first target sub-structure 151 has a first pitch $P_1$ and the first periodic component of the second target sub-structure 153 has a second pitch $P_2$. In the second pair 62 of overlapping target sub-structures 152 and 154, the first periodic component of the first target sub-structure 152 has the second pitch $P_2$ and the first periodic component of the second target substructure 154 has the first pitch $P_1$. It can be seen from inspection of equations 6 that swapping $P_1$ and $P_2$ in this manner results in the target 60 producing a fringe pattern from the first pair 61 of overlapping target sub-structures 151 and 153 that moves in an opposite direction to a fringe pattern from the second pair 62 of overlapping target sub-structures 152 and 154, as a function of overlay error. FIGS. 13 and 14 depict example patterns for a target 60 of this type. FIG. 13 depicts patterns suitable for target sub-structures 153 (right) and 154 (left). FIG. 14 depicts patterns suitable for target sub-structures 151 (right) and 152 (left). FIG. 15 depicts example fringe patterns. The right-hand fringe pattern corresponds to the first pair 161 of overlapping target sub-structures 151 and 153. The left-hand fringe pattern corresponds to the second pair 62 of overlapping target sub-structures 152 and 154.

Figure 33:
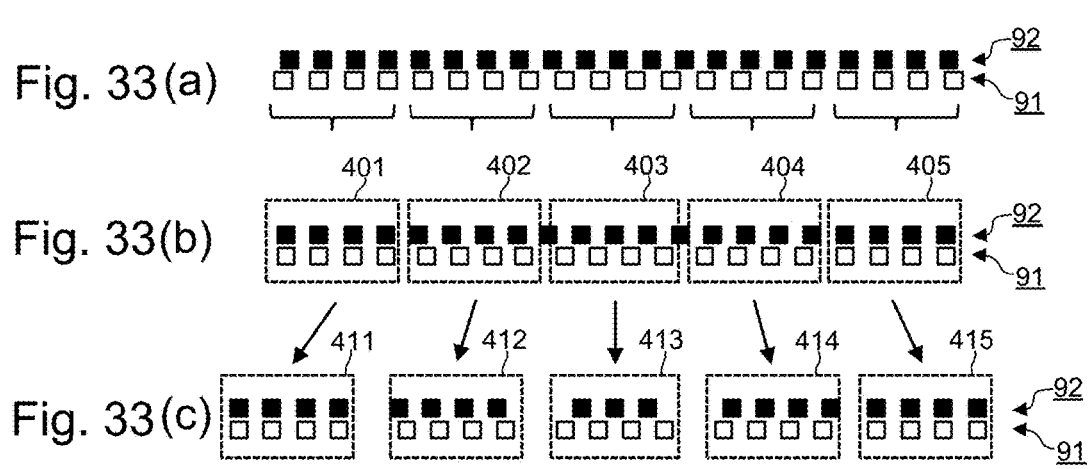
FIGS. 33(a)-33(c) illustrate a correspondence between a method of measuring overlay error using pairs of target sub-structures with common pitch and different overlay bias and a method of measuring overlay error using a pair of target sub-structures with different pitch.

FIG. 33 illustrates a correspondence between a method of measuring overlay error using pairs of target sub-structures with common pitch and different overlay bias (as described above for example with reference to FIGS. 21-27), and a method of measuring overlay error using a pair of target sub-structures with different pitch (as described above for example with reference to FIGS. 28-32). FIG. 33(*a*) shows a portion of an example first target structure 91 having pitch $P_1$ and an example second target structure 92 having pitch $P_2$. The difference in pitch can be exploited to produce a fringe pattern as described above. Overlay error can be extracted from a change in the spatial phase of the fringe pattern. The alternative approach of using multiple pairs of target sub-structures with the same pitch P but different overlay biases can be viewed as effectively sampling the fringe pattern that would be produced using target structures with different pitch. FIG. 33(b) shows example segments 401-405 extracted from the arrangement of FIG. 33(a). Each segment 401-405 will have a different average shift between the portion of the first target structure 91 and second target structure 92 in the segment. Each segment 401-405 could then be approximated by a respective pair of target sub-structures 411-415 which have the same pitch and an overlay bias equal to the average shift of the segment 401-405, as shown in FIG. 33(c). Thus, for example, pair 411 has an overlay bias equal to the average shift in segment 401, pair 412 has an overlay bias equal to the average shift in segment 402, etc. The resulting multiple pairs of sub-structures 411-415 of FIG. 33(c) thus provide an approximation of the full arrangement of FIG. 33(a). Measurement of the intensity values corresponding to the multiple pairs of target sub-structures 411-415 of FIG. 33(c) effectively samples the variation of intensity of the fringe pattern formed directly by the arrangement of FIG. 33(a). A shift in the phase of the fringe pattern can thus be detected. Overlay error proportional to the shift in phase can therefore also be detected.

In an embodiment, as depicted for example in FIG. 32, the target 60 comprises one or more further target structures 93, 94, respectively in one or more further layers 83, 84 of the layered structure. The further target structures 93, 94 are thus provided in addition to the first target structure 91 and second target structures 92 (respectively in layers 81 and 82) of the embodiment discussed above. In such an embodiment, the target 60 comprises at least one pair of overlapping target sub-structures in each of a plurality of different respective pairs of layers of the layered structure. Each of the pairs of overlapping sub-structures that is in a different respective pair of layers of the layered structure comprises first periodic components in which a difference in pitch is different, thereby providing a fringe pattern having a different spatial frequency for each of the different pairs of layers of the layered structure. In the example of FIG. 32, the target structures 91-94 respectively comprise first periodic components having pitches $P_1$-$P_4$. Different pairs of the target structures have different differences in pitch: for example, $P_1$-$P_2 \neq P_1$-$P_3 \neq P_1$-$P_4$ etc. Fringe patterns resulting from the different pairs thus have different spatial frequencies and can therefore be resolved. The different frequencies allow the different fringe frequencies to encode different information, for example a separate overlay value for each different fringe frequency. Overlay errors with respect to different pairs of layers in the target can therefore be obtained simultaneously via a single illumination of one and the same region on the target. Detailed overlay measurements are therefore possible without multiple different targets and/or multiple different measurement steps.

In the embodiment shown a plurality of reference structures R1-R3 provide phase references for each of the pairs of target structures being considered. Reference structure R1 acts as a phase reference with respect to fringes formed by target structures 91 and 92 (e.g. by forming fringes having the same pitch as the fringes formed by the target structures 91 and 92). Reference structure R2 acts as a phase reference with respect to fringes formed by target structures 91 and 93 (e.g. by forming fringes having the same pitch as the fringes formed by the target structures 91 and 93). Reference structure R3 acts as phase reference with respect to fringes formed by target structures 91 and 93 (e.g. by forming fringes having the same pitch as the fringes formed by the target structures 91 and 93). Fewer or additional reference structures may be provided as needed.

In any of the embodiments described above, each pair of target sub-structures may comprise at least one target sub-structure with a second periodic component orientated in a different direction to the first periodic component (i.e. either or both target sub-structures in each pair each comprises such a second periodic component). For example, the second periodic component may be oriented perpendicularly to the second periodic component. The second periodic component acts to separate in the pupil plane (Fourier space), independently from the Fourier components that control the interference fringe phase and frequency, the interfering predetermined diffraction orders from zeroth order scattered radiation, thereby improving the accuracy with which the scattered radiation formed by the interference between the predetermined diffraction orders can be detected. Contamination from zeroth order radiation is reduced. Additionally, the second periodic component changes the angle at which the scattered radiation formed by the interference between the predetermined diffraction orders leaves the target 60 (see FIG. 9-11 for example). The second periodic component can thus be configured to ensure that the angle is appropriate for the detection system of the metrology system (e.g. such that the scattered radiation enters a pupil of the objective lens 16 of the detection system and/or allowing the radiation to be directed to a particular location on a detector array of the detection system). The second periodic component therefore makes it possible simultaneously to have (a) symmetric doubly-diffracted orders within one plane and (b) separation of selected information-carrying orders from the zeroth order in another, typically orthogonal, plane.

The target sub-structure with a second periodic component orientated in a different direction to the first periodic component may take various forms, including one or more of the following: a checkerboard pattern formed from square elements or rectangular elements, a tilted checkerboard pattern formed from square elements or rectangular elements rotated by a predetermined angle about an axis perpendicular to the plane of the checkerboard pattern, and a two-dimensional grating.

Figure 34:
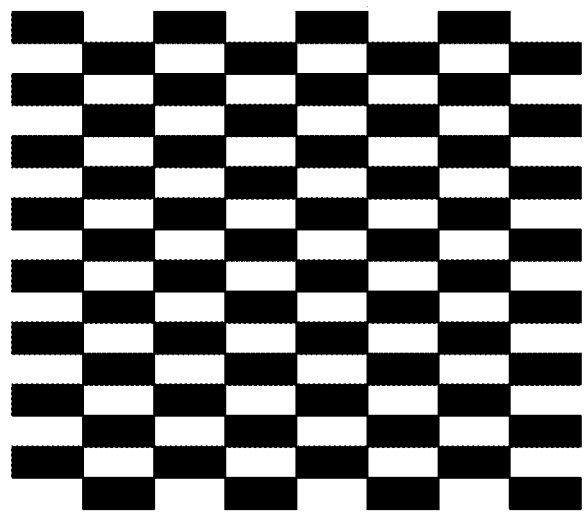
FIG. 34 depicts a checkerboard pattern with rectangular elements.
Figure 35:
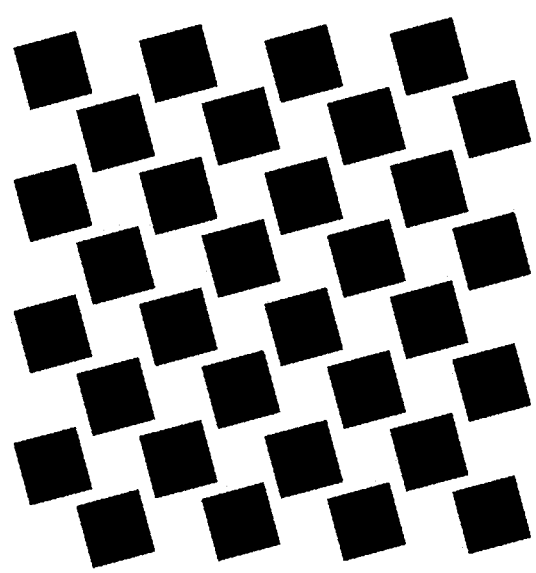
FIG. 35 depicts a tilted checkerboard pattern.

Example checkerboard patterns formed from square elements are shown in FIGS. 14 and 20(b) for example. An example checkerboard pattern formed from rectangular (non-square) elements is shown in FIG. 34. An example tilted checkerboard pattern is shown in FIG. 35. Checkerboard patterns have been found to work particularly effectively because of the relatively low level of unwanted harmonics in the diffraction pattern. The tilted checkerboard pattern may be favored over a regular checkerboard pattern where it is desired to avoid corner-to-corner contacts between elements of the checkerboard. However, other patterns could be used. A variant of the checkerboard pattern in which all of the square elements are aligned along both X and Y could be used for example, as shown in FIG. 20(a). In an alternative embodiment, a pair of target sub-structures is provided in which a top grating has a pitch $P_1$ and a bottom grating has a pitch $P_2$. Gratings lines on the bottom grating are provided at an oblique angle theta relative to the top grating. The bottom grating comprises multiple grating segments. A first set of grating segments comprises grating lines rotated at +theta. A second set of grating segments comprises grating lines rotated at −theta. Alternatively or additionally, the segments from the different sets may be interspersed with respect to each other to form a periodic pattern of equal and oppositely rotated grating segments. The rotated segments produce diffraction at the same angles as the checkerboard but without corner-to-corner contact of the individual structural elements. In a further alternative embodiment, a checkerboard pattern is formed with rounded edges or unequal rectangle-space ratio.

An example of a typical two-dimensional grating is shown in FIG. 20(a) for example.

Further examples of particular target structures are shown in FIGS. 36-39. In each of these figures, the pattern shown in (a) corresponds to a second target structure 92 (top target) and the pattern shown in (b) corresponds to a first target structure 91 (bottom target). The patterns could however be reversed.

Figure 36A:
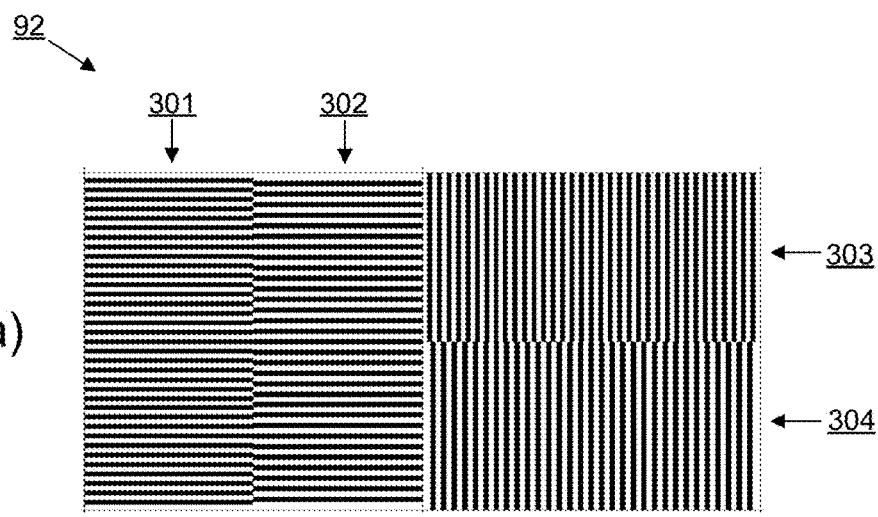
FIGS. 36(a)-36(b), 37(a)-37(b), 38(a)-38(b) and 39(a)-39(b) depict further examples of pairs of target structures.

FIG. 36(a) depicts a second target structure 92 having a footprint within 16 microns along Y (vertical in the figure) and 32 microns along X (horizontal in the figure). These are purely exemplary dimensions. Target sub-structures 301 and 303 are line gratings with pitch ($P_1$)=450 nm. Target sub-structures 302 and 304 are line gratings with pitch ($P_2$)=500 nm.

Figure 36B:
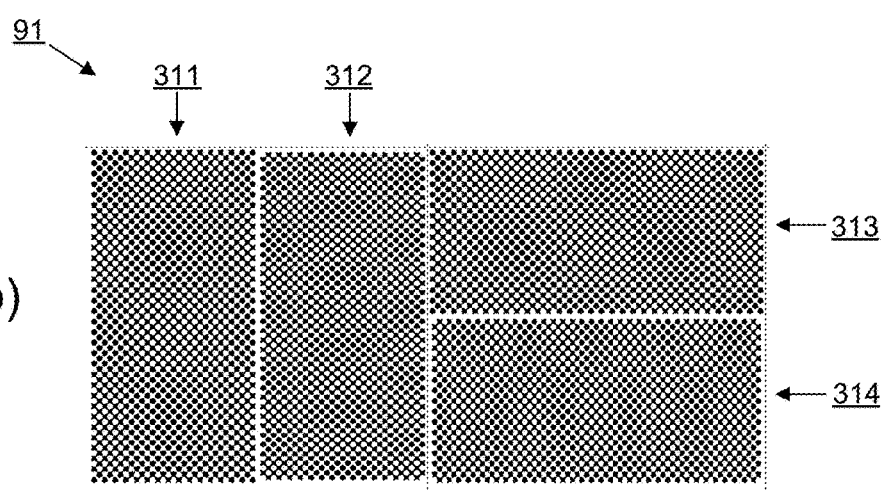

FIG. 36(b) depicts a first target structure 91 configured to form pairs of target sub-structures with the second target structure 92 of FIG. 36(a). Target sub-structures 311 and 313 (which pair respectively with target sub-structures 301 and 303) comprise checkerboard patterns having a pitch ($P_2$) =500 nm parallel to the pitches $P_1$ of target sub-structures 301 and 303, and a pitch ($P_H$)=500 nm in the perpendicular direction. Target substructures 312 and 314 (which pair respectively with target sub-structures 302 and 304) comprise checkerboard patterns having a pitch ($P_1$)=450 nm parallel to the pitches of target sub-structures 302 and 304, and a pitch ($P_H$)=500 nm in the perpendicular direction. Thus, $P_1$=450 nm and $P_2$=500 nm in this example. Target sub-structures 301, 302, 311 and 312 provide sensitivity to overlay errors in the vertical direction in the figure. Target sub-structures 303, 304, 313 and 314 provide sensitivity to overlay errors in the horizontal direction in the figure.

Figure 37A:
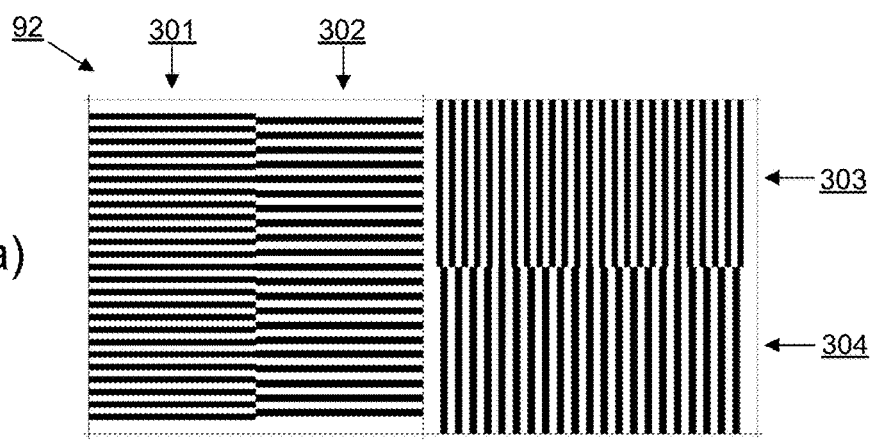
Figure 37B:
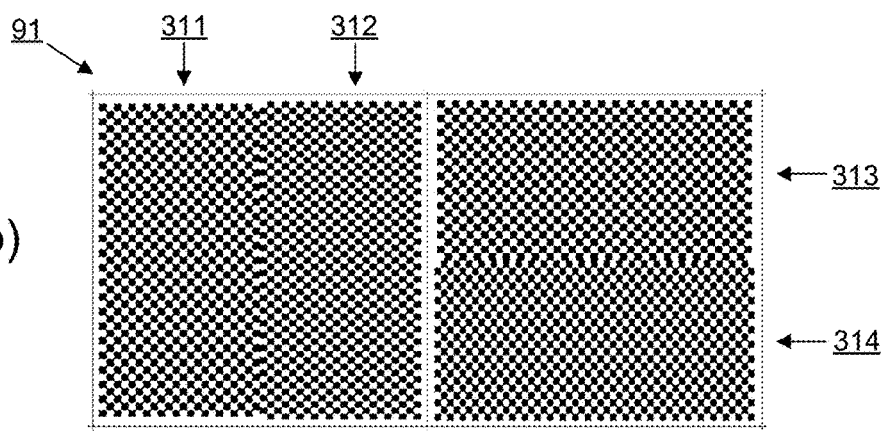

FIG. 37 depicts a second target structure 92 and a first target structure 91 that are the same as in FIG. 36 except that the $P_1$=600 nm, $P_2$=700 nm and $P_H$=700 nm. The values of $P_1$, $P_2$ and $P_H$ in FIGS. 36 and 37 are purely exemplary.

Figure 38A:
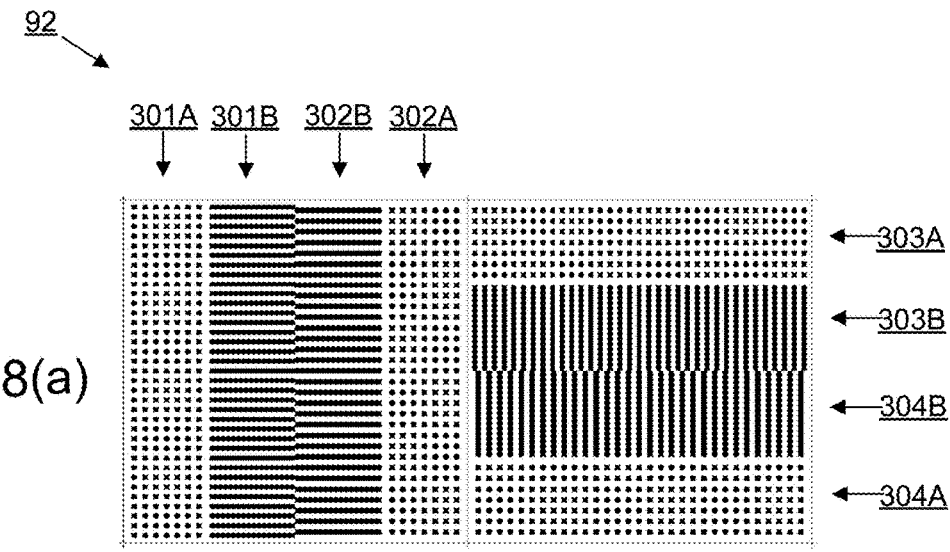

FIG. 38(a) depicts a second target structure 92 having a footprint (purely exemplary) within 16 microns along Y (vertical in the figure) and 32 microns along X (horizontal in the figure). Target sub-structures 301A and 301B comprise gratings having a parallel periodic component with a pitch ($P_1$)=450 nm. Target sub-structures 303A and 303B also comprise gratings having a parallel periodic component with a pitch ($P_1$)=450 nm (perpendicular to 301A and 301B). Outer gratings 301A and 303A additionally comprise a periodicity of pitch ($P_H$)=500 nm in a perpendicular direction.

Target sub-structures 302A and 302B comprise gratings having a parallel periodic component with a pitch ($P_2$)=500 nm. Target sub-structures 304A and 304B also comprise gratings having a parallel periodic component with a pitch ($P_2$)=500 nm (perpendicular to 302A and 302B). Outer gratings 302A and 304A additionally comprise a periodicity of pitch ($P_H$)=500 nm in a perpendicular direction.

The two-dimensional structure of the outer gratings 301A, 302A, 303A and 304A produce twice the fringe period of the inner gratings 301B, 302B, 303B and 304B. Doubling the fringe period can be desirable for reducing phase ambiguity, e.g. in the case that the overlay causes the inner set of fringes (produced by the inner gratings) to have a π phase shift, the outer set of fringes (produced by the outer gratings) would have a π/2 phase shift. The range of unambiguous measurement is thereby increased.

Figure 38B:
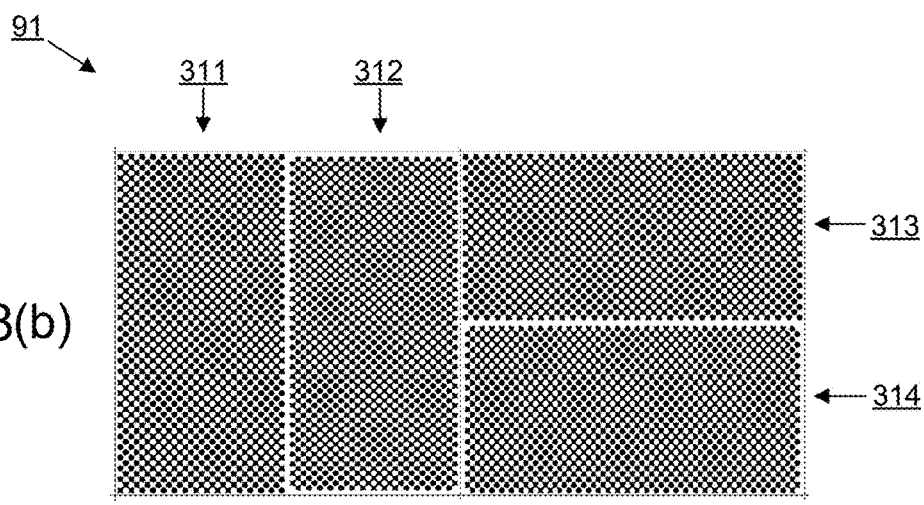

FIG. 38(b) depicts a first target structure 91 configured to form pairs of target sub-structures with the second target structure 92 of FIG. 38(a). Target substructures 311 and 313 comprise checkerboard patterns having a pitch ($P_2$)=500 nm parallel to the pitches ($P_1$) of target sub-structures 301A, 301B, 303A and 303B, and a pitch ($P_H$)=500 nm in the perpendicular direction. Target substructures 312 and 314 comprise checkerboard patterns having a pitch ($P_1$)=450 nm parallel to the pitches ($P_2$) of target sub-structures 302A, 302B, 304A and 304B, and a pitch ($P_H$)=500 nm in the perpendicular direction.

Figure 39A:
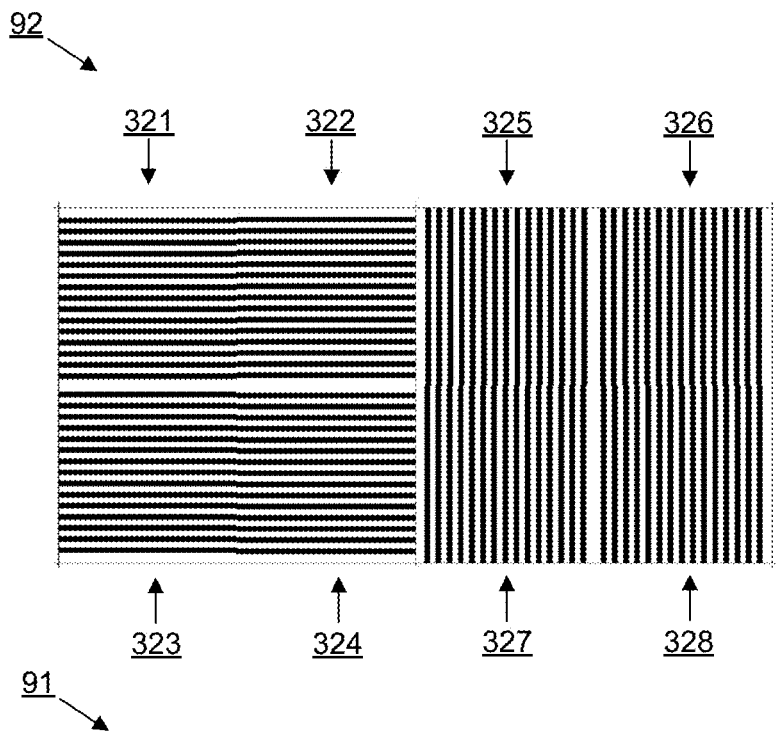

FIG. 39(a) depicts a second target structure 92 having a (purely exemplary) footprint within 16 microns along Y (vertical in the figure) and 32 microns along X (horizontal in the figure). Target sub-structures 321-324 comprise line gratings with the same pitch (P)=500 nm but different overlay biases. The overlay biases are given by −P/8−d, P/8+d, −P/8+d and P/8−d, where d=20 nm, yielding overlay biases of −82.5 nm, −42.5 nm, 42.5 nm and 82.5 nm. Target sub-structures 321-324 provide sensitivity to overlay error in the Y direction (in combination with the first target structure 91). Target sub-structures 325-328 are orientated perpendicularly to the target sub-structures 321-324 but are otherwise the same as the target sub-structures 321-324. Target sub-structures 325-328 thus provide sensitivity to overlay error in the X direction (in combination with the first target structure 91).

Figure 39B:
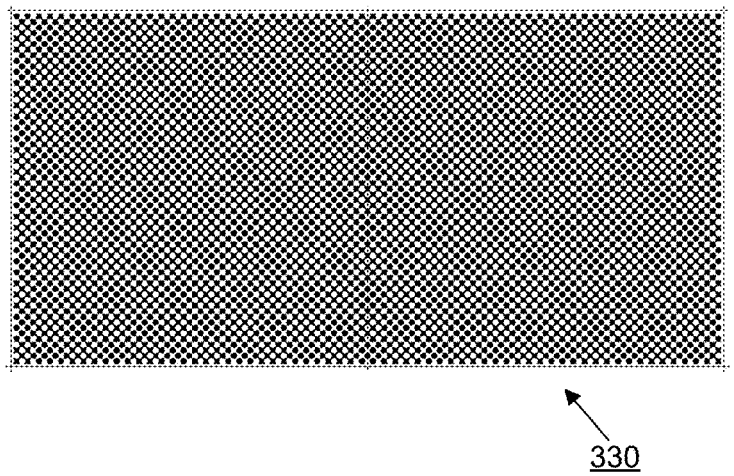

FIG. 39(b) depicts a first target structure 91 configured to form pairs of target sub-structures with the second target structure 92 of FIG. 39(a). Target substructure 330 comprises a checkerboard pattern having a pitch (P)=500 nm parallel to the pitches (P) of target sub-structures 321, 322, 323 and 324, and a pitch ($P_H$)=500 nm in the perpendicular direction (i.e. a checkerboard pattern comprising square elements). The checkerboard pattern also provides a pitch (P)=500 nm parallel to the pitches (P) of target sub-structures 325, 326, 327 and 328, and a pitch ($P_H$)=500 nm in the perpendicular direction.

In an embodiment, a metrology apparatus is provided that is operable to perform any of the methods of measuring a target described above. The metrology apparatus may be configured as described above in FIG. 3(a) for example. An illumination system illuminates with measurement radiation a target 60 produced using a lithographic process on a substrate. A detection system detects scattered radiation arising from illumination of the target 60. The detection system may comprise at least the second measurement branch depicted in FIG. 3(a). The detection system may comprise a sensor 23 that detects the scattered radiation formed by interference between the predetermined diffraction orders.

Further embodiments according to the current invention are provided in below numbered clauses.

I. A method of measuring a characteristic of a lithographic process comprising detecting interfering light scattered from a target comprising at least two overlapping gratings when the target is illuminated with light from an illumination source and calculating a characteristic of a lithographic process independent of the properties of the target.

II. A method according to clause I wherein the calculation is using a signal proportional to the phase of a periodic signal originated from the interfering light.

IIA. A method according any of the preceding clauses wherein the property of the target is a stack thickness.

III. A method of measuring a characteristic of a lithographic process comprising detecting interfering light scattered from a target comprising at least two overlapping gratings when the target is illuminated with light from an illumination source and calculating a characteristic of a lithographic process independent of wavelength of the light from the illuminating source.

IV. A method according to the clause III wherein the calculation is using a signal proportional to the phase of a periodic signal originated from the interfering light.

V. A method of measuring a characteristic of a lithographic process comprising detecting interfering light scattered from a target comprising at least two overlapping gratings when the target is illuminated with light from an illumination source and calculating a characteristic of a lithographic process comprising determining a phase of a periodic signal originated from the interfering light.

VI. A method according to clause V wherein the calculating of a characteristic of a lithographic process is independent of the stack thickness.

VII. A method according any preceding clauses wherein the calculating of a characteristic of a lithographic process is independent of the wavelength of the light used to illuminate the target.

VIII. A method according to any of the preceding clauses wherein the characteristic of the lithographic process is overlay.

Further embodiments according to the invention are described in below numbered clauses:

1. A method of measuring a target formed by a lithographic process, the target comprising a layered structure having a first target structure in a first layer and a second target structure in a second layer, the method comprising:

illuminating the target with measurement radiation;

detecting scattered radiation formed by interference between plural predetermined diffraction orders, wherein the predetermined diffraction orders are generated by diffraction of the measurement radiation from the first target structure and are subsequently diffracted from the second target structure; and calculating a characteristic of the lithographic process using the detected scattered radiation formed by the interference between the predetermined diffraction orders.

2. The method of clause 1, wherein said characteristic of the lithographic process comprises an overlay error between the first target structure and the second target structure.

3. The method of clause 1 or 2, wherein said predetermined diffraction orders comprise two equal and opposite diffraction orders.

4. The method of any of clauses 1-3, wherein:

the predetermined diffraction orders are generated by diffraction in reflection from the first target structure and the subsequent diffraction of the predetermined diffraction orders from the second target structure comprises diffraction in transmission through the second target structure; or the predetermined diffraction orders are generated by diffraction in transmission through the first target structure and the subsequent diffraction of the predetermined diffraction orders from the second target structure comprises diffraction in reflection from the second target structure.

5. The method of any preceding clause, wherein:

the target comprises three or more pairs of overlapping target sub-structures, each pair of overlapping target sub-structures comprising a first target sub-structure in the first target structure and a second target sub-structure in the second target structure;

each of the first target sub-structure and the second target sub-structure in each pair of overlapping target sub-structures comprises a first periodic component having the same pitch and orientation; and each pair of overlapping target sub-structures is provided with a different overlay bias.

6. The method of clause 5, wherein the detected scattered radiation formed by interference between the predetermined diffraction orders comprises a plurality of intensity sub-regions, each intensity sub-region having spatially uniform intensity and being formed by measurement radiation diffracted from a different respective pair of the three or more pairs of target sub-structures, and wherein the calculating of the characteristic of the lithographic process uses a level of intensity in each intensity sub-region to determine the characteristic of the lithographic process.

7. The method of clause 5 or 6, wherein the predetermined diffraction orders are defined with respect to diffraction from the first periodic component in each pair of target sub-structures.

8. The method of any of clauses 5-7, wherein the overlay biases comprise one or more pairs of equal and opposite overlay biases.

9. The method of any of clauses 5-8, wherein the three or more pairs of target sub-structures comprises four pairs of target sub-structures.

10. The method of clause 9, wherein the overlay biases comprise the following: −P/8−d, P/8+d, −P/8+d and P/8−d, where P is the pitch of the first periodic component and d is a predetermined constant.

11. The method of any of clauses 1-4, wherein the detected scattered radiation formed by interference between the predetermined diffraction orders comprises a fringe pattern.

12. The method of clause 11, wherein the calculation of the characteristic of the lithographic process comprises calculating an overlay error between the first target structure and the second target structure by extracting a phase of the fringe pattern.

13. The method of clause 11 or 12, wherein:

the target comprises at least one pair of overlapping target sub-structures, each pair of overlapping target sub-structures comprising a first target sub-structure in the first target structure and a second target sub-structure in the second target structure; and each of the first target sub-structure and the second target sub-structure in each pair of overlapping target sub-structures comprises a first periodic component having the same orientation and a different pitch.

14. The method of clause 13, wherein the detected scattered radiation formed by interference between the predetermined diffraction orders comprises a fringe pattern formed by each pair of target sub-structures.

15. The method of clause 14, wherein the target further comprises a reference structure configured to provide a radiation pattern having the same periodicity as the fringe pattern, wherein the reference structure is provided in such a way that there is substantially no positional shift of fringes in the radiation pattern as a function of overlay error between the first target structure and the second target structure.

16. The method of any of clauses 13-15, wherein:

the target comprises at least a first pair of overlapping target sub-structures and a second pair of overlapping target sub-structures;

in the first pair of overlapping target sub-structures, the first periodic component of the first target sub-structure has a first pitch and the first periodic component of the second target substructure has a second pitch; and in the second pair of overlapping target sub-structures, the first periodic component of the first target sub-structure has the second pitch and the first periodic component of the second target sub-structure has the first pitch.

17. The method of any of clauses 11-16, wherein:

the target comprises one or more further target structures respectively in one or more further layers of the layered structure;

the target comprises at least one pair of overlapping target sub-structures in each of a plurality of different respective pairs of layers of the layered structure, wherein each of the pairs of overlapping sub-structures that is in a different respective pair of layers of the layered structure comprises first periodic components in which a difference in pitch is different, thereby providing a fringe pattern having a different spatial frequency for each of the different pairs of layers of the layered structure.

18. The method of any of clauses 5-17, wherein either or both target sub-structures in each of the pairs of target sub-structures each comprises a second periodic component orientated in a different direction to the first periodic component.

19. The method of clause 18, wherein the first periodic component is orientated perpendicularly to the second periodic component.

20. The method of clause 18 or 19, wherein the target sub-structure with a second periodic component orientated in a different direction to the first periodic component comprises one or more of the following: a checkerboard pattern formed from square elements or rectangular elements, a tilted checkerboard pattern formed from square elements or rectangular elements rotated by a predetermined angle about an axis perpendicular to the plane of the checkerboard pattern, and a two-dimensional grating.

21. A substrate comprising a target formed by a lithographic process, the target comprising a layered structure having a first target structure in a first layer and a second target structure in a second layer, wherein the first target structure and the second target structure are configured to allow detection of radiation scattered from the target when the target is illuminated with measurement radiation, the detected scattered radiation being formed by interference between plural predetermined diffraction orders, wherein the predetermined diffraction orders are generated by diffraction of the measurement radiation from the first target structure and are subsequently diffracted from the second target structure.

22. The substrate of clause 21, wherein the target is an overlay target for measurement of overlay error, the overlay target being configured such that the detected scattered radiation formed by interference between the predetermined diffraction orders varies as a function of overlay error between the first target structure and the second target structure.

23. A metrology apparatus comprising:

an illumination system configured to illuminate with measurement radiation a target produced using a lithographic process on a substrate; and a detection system configured to detect scattered radiation arising from illumination of the target, wherein:

the metrology apparatus is operable to perform the method of any of clauses 1-20.

24. A lithographic apparatus configured to produce the substrate of clause 21 or 22 by forming the target on the substrate.

While the targets described above are metrology targets specifically designed and formed for the purposes of measurement, in other embodiments, properties may be measured on targets which are functional parts of devices formed on the substrate. Many devices have regular, grating-like structures. The terms 'target grating' and 'target' as used herein do not require that the structure has been provided specifically for the measurement being performed. Further, pitch P of the metrology targets is close to the resolution limit of the optical system of the scatterometer, but may be much larger than the dimension of typical product features made by lithographic process in the target portions C. In practice the lines and/or spaces of the overlay gratings within the targets may be made to include smaller structures similar in dimension to the product features.

In association with the physical grating structures of the targets as realized on substrates and patterning devices, an embodiment may include a computer program containing one or more sequences of machine-readable instructions describing methods of measuring targets on a substrate and/or analyzing measurements to obtain information about a lithographic process. This computer program may be executed for example within unit PU in the apparatus of FIG. 3 and/or the control unit LACU of FIG. 2. There may also be provided a data storage medium (e.g., semiconductor memory, magnetic or optical disk) having such a computer program stored therein. Where an existing metrology apparatus, for example of the type shown in FIG. 3, is already in production and/or in use, the invention can be implemented by the provision of updated computer program products for causing a processor to perform the modified step S6 and so calculate overlay error or other parameters with reduced sensitivity to structural asymmetry.

The program may optionally be arranged to control the optical system, substrate support and the like to perform the steps S2-S5 for measurement of asymmetry on a suitable plurality of targets.

While the embodiments disclosed above are described in terms of diffraction based overlay measurements (e.g., measurements made using the second measurement branch of the apparatus shown in FIG. 3(a)), in principle the same models can be used for pupil based overlay measurements (e.g., measurements made using the first measurement branch of the apparatus shown in FIG. 3(a)). Consequently, it should be appreciated that the concepts described herein are equally applicable to diffraction based overlay measurements and pupil based overlay measurements.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of measuring a target formed by a lithographic process, the target comprising a layered structure having a first target structure in a first layer and a second target structure in a second layer, the method comprising:
   illuminating the target with measurement radiation;
   detecting scattered radiation formed by interference between plural predetermined diffraction orders, wherein the predetermined diffraction orders are generated by double diffraction of the measurement radiation from the first target structure and the second target structure; and
   calculating a characteristic of the lithographic process using the detected scattered radiation formed by the interference between the predetermined diffraction orders;
   wherein the first target structure includes a two-dimensional periodic component,
   wherein the second target structure includes a one-dimensional periodic component, and
   wherein the one-dimensional periodic component overlaps the two-dimensional periodic component.

2. The method of claim 1, wherein said characteristic of the lithographic process comprises an overlay error between the first target structure and the second target structure.

3. The method of claim 1, wherein said predetermined diffraction orders comprise two equal and opposite diffraction orders.

4. The method of claim 1, wherein:
   the predetermined diffraction orders are generated by diffraction in reflection from the first target structure and the subsequent diffraction of the predetermined diffraction orders from the second target structure comprises diffraction in transmission through the second target structure; or
   the predetermined diffraction orders are generated by diffraction in transmission through the first target structure and the subsequent diffraction of the predetermined diffraction orders from the second target structure comprises diffraction in reflection from the second target structure.

5. The method of claim 1, wherein:
   the target comprises three or more pairs of overlapping target sub-structures, each pair of overlapping target sub-structures comprising a first target sub-structure in the first target structure and a second target sub-structure in the second target structure;
   each of the first target sub-structure and the second target sub-structure in each pair of overlapping target sub-structures comprises a first periodic component having the same pitch and orientation; and
   each pair of overlapping target sub-structures is provided with a different overlay bias.

6. The method of claim 5, wherein:
   the detected scattered radiation formed by interference between the predetermined diffraction orders comprises a plurality of intensity sub-regions, each intensity sub-region having spatially uniform intensity and being formed by measurement radiation diffracted from a different respective pair of the three or more pairs of target sub-structures, and
   the calculating of the characteristic of the lithographic process uses a level of intensity in each intensity sub-region to determine the characteristic of the lithographic process.

7. The method of claim 5, wherein the predetermined diffraction orders are defined with respect to diffraction from the first periodic component in each pair of target sub-structures.

8. The method of claim 5, wherein the overlay biases comprise one or more pairs of equal and opposite overlay biases.

9. The method of claim 5, wherein the three or more pairs of target sub-structures comprises four pairs of target sub-structures.

10. The method of claim 9, wherein the overlay biases comprise the following: $-P8-d$, $P8+d$, $-P8+d$ and $P8-d$, where P is the pitch of the first periodic component and d is a predetermined constant.

11. The method of claim 5, wherein either or both target sub-structures in each of the pairs of target sub-structures each comprises a second periodic component orientated in a different direction to the first periodic component.

12. The method of claim 11, wherein the first periodic component is orientated perpendicularly to the second periodic component.

13. The method of claim 11, wherein the target sub-structure with a second periodic component orientated in a different direction to the first periodic component comprises one or more of the following:
   a checkerboard pattern formed from square elements or rectangular elements,
   a tilted checkerboard pattern formed from square elements or rectangular elements rotated by a predetermined angle about an axis perpendicular to the plane of the checkerboard pattern, and
   a two-dimensional grating.

14. The method of claim 1, wherein the detected scattered radiation formed by interference between the predetermined diffraction orders comprises a fringe pattern.

15. The method of claim 14, wherein the calculation of the characteristic of the lithographic process comprises calculating an overlay error between the first target structure and the second target structure by extracting a phase of the fringe pattern.

16. The method of claim 1, wherein the predetermined diffraction orders are further generated by diffraction of the measurement radiation from the first target structure component and subsequent diffraction from the second first target structure.

17. The method of claim 1, wherein the predetermined diffraction orders are generated by diffraction of the measurement radiation from the second target structure and are subsequently diffracted from the first target structure.

18. A substrate comprising:
   a target formed by a lithographic process, the target comprising:
      a layered structure having a first target structure in a first layer and a second target structure in a second layer,
      wherein the first target structure includes a two-dimensional periodic component,
      wherein the second target structure includes a one-dimensional periodic component, and
      wherein the one-dimensional periodic component overlaps the two-dimensional periodic component,
      wherein the first target structure and the second target structure are configured to allow detection of radiation scattered from the target when the target is illuminated with measurement radiation, the detected scattered radiation being formed by interference between plural predetermined diffraction orders,
      wherein the predetermined diffraction orders are generated by double diffraction of the measurement radiation from the first target structure and the second target structure.

19. The substrate of claim 18, wherein the target is an overlay target for measurement of overlay error, the overlay target being configured such that the detected scattered radiation formed by interference between the predetermined diffraction orders varies as a function of overlay error between the first target structure and the second target structure.

20. A lithographic apparatus configured to produce the substrate of claim 18 by forming the target on the substrate.

21. A metrology apparatus comprising:
   an illumination system configured to illuminate with measurement radiation a target produced using a lithographic process on a substrate; and
   a detection system configured to detect scattered radiation arising from illumination of the target, wherein:
      the metrology apparatus is operable to perform a method of measuring the target formed by the lithographic process, the target comprising a layered structure having a first target structure in a first layer and a second target structure in a second layer, the method comprising:
         illuminating the target with the measurement radiation;
         detecting scattered radiation formed by interference between plural predetermined diffraction orders, wherein the predetermined diffraction orders are generated by double diffraction of the measurement radiation from the first target structure and the second target structure; and
         calculating a characteristic of the lithographic process using the detected scattered radiation formed by the interference between the predetermined diffraction orders;
      wherein the first target structure includes a two-dimensional periodic component,
      wherein the second target structure includes a one-dimensional periodic component, and
      wherein the one-dimensional periodic component overlaps the two-dimensional periodic component.

* * * * *